United States Patent [19]

Hammock et al.

[11] Patent Number: 5,674,747

[45] Date of Patent: *Oct. 7, 1997

[54] VIRAL VECTOR CODING FOR JUVENILE HORMONE ESTERASE

[75] Inventors: Bruce D. Hammock, Davis, Calif.; Terry N. Hanzlik, Chapman, Australia; Lawrence G. Harshman, Dixon, Calif.; Bryony C. Bonning; Vernon K. Ward, both of Davis, Calif.

[73] Assignee: The Regents of the University of California, Oakland, Calif.

[*] Notice: The term of this patent shall not extend beyond the expiration date of Pat. No. 5,098,706.

[21] Appl. No.: 440,520

[22] Filed: May 12, 1995

Related U.S. Application Data

[60] Division of Ser. No. 927,851, Aug. 10, 1992, Pat. No. 5,643,776, which is a continuation-in-part of Ser. No. 725,226, Jun. 26, 1991, abandoned, which is a continuation of Ser. No. 265,507, Nov. 1, 1988, abandoned.

[51] Int. Cl.[6] .......................... C12N 15/86; C12N 15/52
[52] U.S. Cl. .......................... 435/320.1; 435/172.3; 435/196; 435/348; 424/93.2
[58] Field of Search .................. 424/93.2; 435/196, 435/172.3, 240.1, 240.2, 252.3, 348; 536/23.2; 800/2

[56] References Cited

U.S. PATENT DOCUMENTS

| | | | |
|---|---|---|---|
| 4,668,511 | 5/1987 | Aspirot et al. | 424/93.6 |
| 4,745,051 | 5/1988 | Smith et al. | 435/69.51 |
| 4,762,547 | 8/1988 | Iwasaki et al. | 504/330 |
| 4,870,023 | 9/1989 | Fraser et al. | 435/235.1 |
| 4,888,340 | 12/1989 | Neh et al. | 514/403 |
| 4,929,718 | 5/1990 | Possani et al. | 530/326 |
| 5,071,748 | 12/1991 | Miller | 435/69.1 |
| 5,098,706 | 3/1992 | Hammoch et al. | 424/93 A |
| 5,162,308 | 11/1992 | Brown et al. | 514/63 |
| 5,177,308 | 1/1993 | Barton et al. | 800/205 |
| 5,180,581 | 1/1993 | Miller et al. | 424/93.2 |
| 5,238,724 | 8/1993 | Bjostad, III et al. | 424/84 |
| 5,266,314 | 11/1993 | Maeda | 424/93.2 |
| 5,266,317 | 11/1993 | Tomalski et al. | 424/93.2 |

FOREIGN PATENT DOCUMENTS

| | | |
|---|---|---|
| 0222412B | 11/1986 | European Pat. Off. |
| 0225777A | 12/1986 | European Pat. Off. |
| 2074868 | 3/1981 | United Kingdom |

OTHER PUBLICATIONS

Moffat, Anne Simon, "New Chemicals Seek to Outwit Insect Pests," *Science*, 261, pp. 550–551 (1993).

Hammock et al., "The Role of Juvenile Hormone Metabolism in the Metamorphosis of Selected Lepidoptera," *Chemical Abstracts*, 102 (1985), entry 76006b.

Abdel–Aal and Hammock, "3–Octylthio–1,1,1–trifluoro–2–propanone, A High Affinity and Slow Binding Inhibitor of Juvenile Hormone Esterase from *Trichoplusia ni* (Hüber)," *Insect Biochem.*, 15:1 (1985), pp. 111–122.

Abdel–Aal and Hammock, "Transition State Analogs as Ligands for Affinity Purification of Juvenile Hormone Esterase," *Science*, 233 (Sep. 1986), pp. 1073–1076.

Bachmair and Varshavsky, "The Degradation Signal in a Short–Lived Protein," *Cell*, 56 (Mar. 1989), pp. 1019–1032.

Cheung and Hammock, "Micro–Lipid–Droplet Encapsulation of *Bacillus thuringiensis subsp. israelensis* δ–Endotoxin for Control of Mosquito Larvae," *Appl. & Environ. Microbiol.*, 50:4 (Oct. 1985), pp. 984–988.

Chiang and Dice, "Peptide Sequences that Target Proteins for Enhanced Degradation During Serum Withdrawal," *J. of Biol. Chem.*, 263:14 (May 1988), pp. 6797–6805.

Hammock and Sparks, "A Rapid Assay for Insect Juvenile Hormone Esterase Activity," *Analytical Biochemistry*, 82 (1977), pp. 573–579.

Hammock et al., "Expression and Effects of the Juvenile Hormone Esterase in a Baculovirus Vector," *Nature*, 344:6265 (Mar. 1990), pp. 458–461.

Hammock and Rose, "Analysis of Juvenile Hormone Esterase Activity," Chpt. 32, pp. 487–495 in Law et al. (Eds.), *Methods in Enzymology*, vol. III: *Steroids and Isoprenoids* (Part B), Academic Press (1985).

Hammock et al., "Trifluoromethylketones as Possible Transition State Analog Inhibitors of Juvenile Hormone Esterase," *Pesticide Biochem. & Physiology*, 17 (1982), pp. 76–88.

Hammock et al., "Selective Inhibition of JH Esterases from Cockroach Hemolymph," *Pesticide Biochem. & Physiology*, 7 (1977), pp. 517–530.

Hammock et al., "Strategies for the Discovery of Insect Control Agents: . . . " Chpt. 12 in Steffens et al. (Eds), *Biomechanism Regulating Growth & Development*, USDA Beltsville Symp. vol. 12, Kluwer Academic Press (1988).

Hanzlik et al., "Isolation and Sequencing of cDNA Clones Coding for Juvenile Hormone Esterase from *Heliothis virescens*," *J. of Biol. Chem.*, 264:21 (Jul. 1989), pp. 12419–12425.

Hanzlik and Hammock, "Characterization of Affinity–purified Juvenile Hormone Esterase from *Trichoplusia ni*," *J. Biol. Chem.*, 1987:23 (Oct. 1987), pp. 12584–13591.

(List continued on next page.)

Primary Examiner—John L. LeGuyader
Attorney, Agent, or Firm—Majestic, Parsons, Siebert & Hsue

[57] ABSTRACT

A diagnostic or control composition is useful to characterize or control insects and comprises a nucleotide sequence coding for juvenile hormone esterase (JHE). The coding sequence may be combined with a promoter sequence regulating the transcription thereof in a recombinant expression vector for use in controlling insects having a juvenile hormone esterase dependency. Preferred embodiments of the invention are recombinant baculoviruses in which a mutated JHE coding sequence provides relatively rapid speed of kill in insects.

4 Claims, 4 Drawing Sheets

OTHER PUBLICATIONS

Huynh et al., "Constructing and Screening cDNA Libraries in λgt10 and λgt11," Chpt. 2, IRL Press (Oxford), (1985), pp. 49–78.

Ichinose et al., "Pharmacokinetic Studies of the Recombinant Juvenile Hormone Esterase in *Manduca sexta*, *Pesticide Biochem. & Physiology*", 42 (1992), pp. 13–23.

Ichinose et al., "Uptake of Juvenile Hormone Esterase by Pericardial Cells of *Manduca sexta*," submitted to *Insect Biochem. Molec. Biol.* (1992).

McCutchen et al., "Development of a Recombinant Baculovirus Expressing an Insect–Selective Neurotoxin: Potential for Pest Control," *Bio/Technology*, 9 (Sep. 1991), pp. 848–852.

Philpott and Hammock, "Juvenile Hormone Esterase is a Biochemical Anti–Juvenile Hormone Agent," *Insect Biochem.*, 20:5 (1990), pp. 451–459.

Rogers et al., "Amine Acid Sequences Common to Rapidly Degraded Proteins: The PEST Hypothesis," *Science*, 234 (Oct. 1986), pp. 364–368.

Sparks and Hammock, "Induction and Regulation of Juvenile Hormone Esterases During the Last Larval Instar of the Cabbage Looper, *Trichoplusia ni*," *J. Insect. Physiolo.*, 25 (1979), pp. 551–560.

Sparks and Hammock, "Comparative Inhibition of the Juvenile Hormone Esterases from *Trichoplusia ni*, *Tenebrio molitor*, and *Musca domestica*," *Pesticide Biochem. & Physiology*, 14 (1980), pp. 290–302.

Wozniak and Jones, "Immunochemical Characterization of Juvenile Hormone Esterase from Different Species of *Lepidoptera*," *Biochem. & Biophys. Res. Commun.*, 144:3 (May 1987), pp. 1281–1286.

Wroblewski et al., "Regulation of Juvenile Hormone Esterase Gene Expression in the Tobacco Budworm (*Heliothis virescens*)," *Archives of Biochem. & Biophys.*, 278:2 (May 1990), pp. 461–466.

Eldridge et al., "Insecticidal Properties of Genetically Engineered Baculoviruses Expressing an Insect Juvenile Hormone Esterase Gene," *Appl. & Environ. Microbiol.*, 58:5 (May 1992), pp. 1583–1591.

Hayakawa, "Structure of a Growth–Blocking Peptide Present in Parasitized Insect Hemolymph," *J. of Biol. Chem.*, 266:13 (May 5, 1991), pp. 7982–7984.

Hayakawa, "A Putative New Juvenile Peptide Hormone in Lepidopteran Insects," *Biochemical and Biophysical Research Communications*, 185:3 (Jun. 30, 1993), pp. 1141–1147.

Smith et al., "Production of Human Beta Interferon in Insect Cells Infected with a Baculovirus Expression Vector," *Mol. Cell Biol.*, 3 (1983), pp. 2156–2165.

Betana et al., "Potential of Baculo Viruses Expressing a Scorpion Toxin and an Esterase in Agriculture . . . ," *Abstr. Pap. Am. Chem. Soc.*, (206 Meet., Pt. 1, AGR0122), 1993 (Abstract only).

Hayakawa, "Juvenile Hormone Esterase Activity Repressive Factor in the Plasma of Parasitized Insect Larvae," *J. Biol. Chem.*, 265:19 (1990), pp. 10812–10816.

Hayakawa, "Juvenile Hormone Esterase Activity Repressive Peptide in the Parasitized Armyworm Hemolymph," *Zool. Sci.* (Toyko), 7:6 (1990), p. 1061 (Abstract only).

Ward et al., "Analaysis of the Catalytic Mechanism of Juvenile Hormone Esterase by Site–Directed Mutagenesis," *Int. J. Biochem.* (England), 24:12 (Dec 1993), pp. 1933–1941 (Abstract only).

Hammock et al., "Development of Recombinant Viral Insecticides by Expression of an Insect–Speicfic Toxin . . . ," *Arch. Insect Biochem. Physiol.* (US), 22:3–4 (1993), pp. 315–344 (Abstract only).

Possee et al., "Expression of the Proteins with Insecticidal Activities Using Baculo Virus Vectors . . . ," *Ann. N.Y. Acad. Sci.*, 646 (1991), pp. 234–239 (Abstract only).

Hammock et al., "Improving the Efficacy of Baculo Virus Insecticides by Expressing with Insect Selective Proteins," *Abstr. Pap. Am. Chem. Soc.* (202 Meet., Pt. 1, AGR09) (1991) (Abstract only).

Bonning et al., "Further Development of a Recombinant Baculovirus Insecticide Expressing the Enzyme JHE from Heliothis–Virescens," *Biochem. Mol. Biol.*, 22:5 (1992) pp. 453–458 (Abstract only).

Piek et al., "The Pharmacology of Microbracon Venom," *Comp. Biochem. Physiol.*, vol. 72C, pp. 303–309 (1982).

Miller et al., "Bacterial, Viral, and Fungal Insecticides," *Science*, 219, pp. 715–721, (Feb. 11, 1983).

Sakurai et al., "Complete Nucleotide Sequence of Gene for Sex–Specific Storage Protein of *Bombyx mori*," *Nucleic Acids Research*, 16:15, pp. 7717–7718 (1988).

Merryweather et al., "Construction of Genetically Engineered Baculovirus Insecticides Containning the *Bacillus thuringiensis* subsp. kurstaki HD–73 Delta Endotoxin," *J. of Gen. Virol.*, 71, pp. 1535–1544 (1990).

Martens et al., "Insecticidal Activity of a Bacterial Crystal Protein Expressed by a Recombinant Baculovirus in Insect Cells," *Applied and Environmental Microbiology*, 56:9, pp. 2764–2770, (Sep. 1990).

Tomalski and Miller, "Insect Paralysis by Baculovirus–Mediated Expression of a Mite Neurotoxin Gene," *Nature*, 352, pp. 82–85, (Jul. 4, 1991).

Zlotkin, "Toxins Derived from Arthropod Venoms Specifically Affecting Insects," Chpt. 15 in *Comprehensive Insect Physiology, Biochemistry & Pharmacology*, vol. 10, pp. 499–541 (1985).

Gordon et al., "The Binding of the insect Selective Neurotoxin (AaIT) from Scorpion Venom to Locust Synaptosomal Membranes," *Biochimica et Biophysica Acta*, 778, pp. 349–358 (1984).

Stewart et al., "Construction of an Improved Baculovirus Insecticide Containing an Insect–Specific Toxin Gene," *Nature*, 352, pp. 85–88, (Jul. 4, 1991).

McCutchen et al., "Development of Surrogate Substrates for Juvenile Hormone Esterase," *Archives of Biochemistry and Biophysics*, 307:2 (Dec. 1993), pp. 231–241.

Abdel–Aal and Hammock, "Apparent Multiple Catalytic Sites Involved in the Ester Hydrolysis of Juvenile Hormones by the Hemolymph and . . . ," *Arch. Biochem. Biophys.*, 243:1, (1985), pp. 206–219.

Maeda et al., "Insecticidal Effects of an Insect–Specific Neurotoxin Expressed by a Recombinant Baculovirus," *Virology*, 184 (1991), pp. 777–780.

Touhara et al., "Ligand Binding by a Recombinant Insect Juvenile Hormone Binding Protein," *Biochem.*, 32:8 (1993), pp. 2068–2075.

McCutchen et al., "Recombinant Baculovirus Expressing an Insect–selective Neurotoxin: . . . ," in *Natural & Engineered Pest Management Agents* (Hedin et al., eds), ACS Sympo. Series #551, Am. Chem. Soc., (1994) pp. 348–367.

Heinz et al., "Direct Effects of Recombinant Nuclear Polyhedrosis Viruses on Selected Non–Target Organisms," *J. Econ. Entomol.*, 88:2, (1995), pp. 259–264.

Hammock, "Recombinant Baculoviruses as Biological Insecticides," in *Pest Management: Biolgoically Based Technologies* (Lumsden and Vaughn, eds.), ACS Series, Am. Chem. Soc., (1993), pp. 313–325.

Bonning and Hammock, "Lethal Ratios: An Optimized Strategy for Presentation of Binassay Data Generated from Genetically Engineered Baculoviruses," *J. Invert. Pathol.*, 62 (1993), pp. 196–197.

Maeda et al., "Recombinant Baculoviruses Expressing Foreign Genes for . . . ." in *Pest Control with Enhanced Environmental Safety*, (Duke et al., eds.), ACS Sympos. Series #524, Am. Chem. Soc. (1993), ep. 281–297.

Bonning and Hammock, "Development and Potential of Genetically Engineered Viral Insecticides," *Biotechnol. Genetic Engeinnering Rev.*, 10 (1992), pp. 455–489.

Hammock et al., "Cloning, Expression and Biolgoical Activity of the JHE from *Heliothis virescens*," in *Molecular Insect Science* (Hagedorn et al., eds.) Plenum Press (1990), pp. 49–56.

Bonning et al., "Superior Expression of JHE and α-Galactosidase from the Basic Protein Promoter of *Autographa californica* Nuclear Polyhedrosis Virus Compared to the . . . ." *J. Gen. Virol.*, 75 (1994), pp. 1551–1556.

Harshman et al., "Cloning, Characterization and Genetics of the JHE Gene from *Heliothis virescens*," *Insect. Biochem. Molec. Biol.*, 24:7 (1994), pp. 671–676.

Ichinose et al., "Pharmacokinetics and Tissue Uptake of the Recombinant JHE in Insects" in *Pesticides/Environment:* . . . , (Mitsui et al., eds.), Proc. of 1st Int'l. Symp. on Pest. Sci., Pesticide Sci. Soc. of JP (1993).

Bonning et al., "Insect Control by Use of Recombinant Baculoviruses Expressing JHE," in *Natural and Engineered Pest Management Agents* (Hedin et al., eds.), ACS Symp. Ser. #551, Am. Chem. Soc. (1994), pp. 368–383.

Roelvink et al., "Dissimilar Expression of *Autographa californica* Multiple Nucleocapsid Nuclear Polyhedrosis Virus Polyhedrin and p10 Gene," *J. Gen. Virol.*, 73 (1992), pp. 1481–1489.

Booth et al., "Localization of JHE During Development in Normal and in Recombinant Baculovirus–Infected Larvae of the Moth *Trichoplusia ni, Tissue & Cell*", 24:2 (1992), pp. 267–282.

Harshman et al., "Effects of Recombinant Juvenile Hormone Esterase on *Aedes aegypti*," *Proc. Calif. Mosq. Vector Control Assoc.*, (1991), pp. 77–80.

Hammock, "Regulation of Juvenile Hormone Titer: Degradation," in *Comprehensive Insect Physiology, Biochemistry, and Pharmacology* (Kerkut and Gilbert, eds.) Pergamon Press (1985), pp. 431–472.

Jones and Hammock, "Prepupal Regulation of Juvenile Hormone Esterase through Direct Induction by Juvenile Hormone," *J. Insect Physiol.*, 29:6, (1983), pp. 471–475.

Sparks and Hammock, "A Comparison of the Induced and Naturally Occurring Juvenile Hormone Esterases from Last Instar Larvae of *Trichoplusia ni*," *Insect Biochem.*, 9, (1979), pp. 411–421.

Sparks et al., "Effects of the Anti Hormone–Hormone Mimic ETB on the Inductio nof Insect Juvenile Hormone Esterase in *Trichoplusia ni*", *Life Sci.*, 25 (1979), pp. 445–450.

Zlotkin et al., "The Effect of Scorpion Venom on Blowfly Larvae—A New Method for the Evaluation of Scorpion Venoms Potency," *Toxicon*, 9 (1971), pp. 1–8.

Zlotkin et al., "An Excitatory and a Depressant Insect Toxin from Scorpion Venom both Affect Sodium Conductance and Possess a Common Binding Site," *Arch. Biochem. & Biophys.*, 240:2 (Aug. 1985), pp. 877–887.

Adachi et al., "cDNA Structure and Expressio nof Bombyxin, an Insulin–like Brain Secretory Peptide of the Silkworm *Bombyx mori*," *J. Biol. Chem.*, 264:13 (1984), pp. 349–358.

Maeda, "Increased Insecticidal Effect by a Recombinant Baculovirus Carrying a Synthetic Diuretic Hormone Gene," *Biochem. & Biophys. Res. Comm.*, 165:3 (1989), pp. 1177–1183.

Carbonell et al., "Synthesis of a Gene Coding for an Insect–Specific Scorpion Neurotoxin and Attempts to Express it Using Baculovirus Vectors," *Gene*, 73, pp. 409–418 (1988).

Carbonell et al., "Baculovirus Interaction with Nontarget Organisms: a Virus–Borne Reporter Gene is Not Expressed in Two Mammalian Cell Lines," *Appl.Environ. Microbiol*, 53:7 (Jul. 1987), pp. 1412–1417.

Dee et al., "Expression and Secretion of a Functional Scorpion Insecticidal Toxin in Cultured Mouse Cells," *Bio/Technology*, 8, (Apr.1990) pp. 339–342.

Cameron et al., "Insect Cell Culture Technology in Baculovirus Expression Systems," *Trends in Biotechnology*, vol. 7 (1989), pp. 66–70.

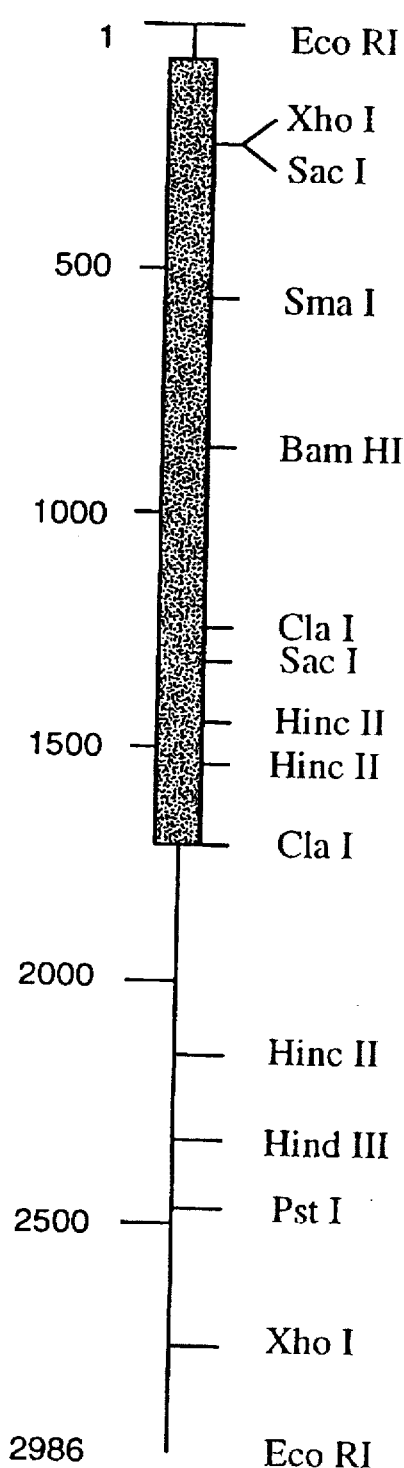
FIG._1
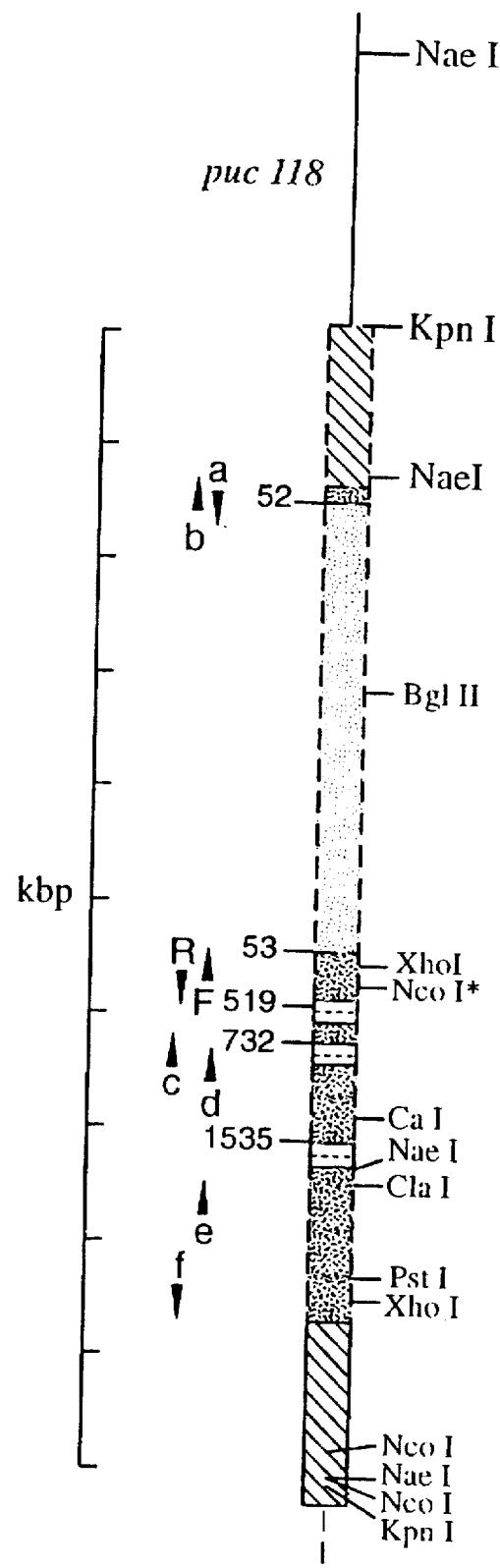
FIG._6

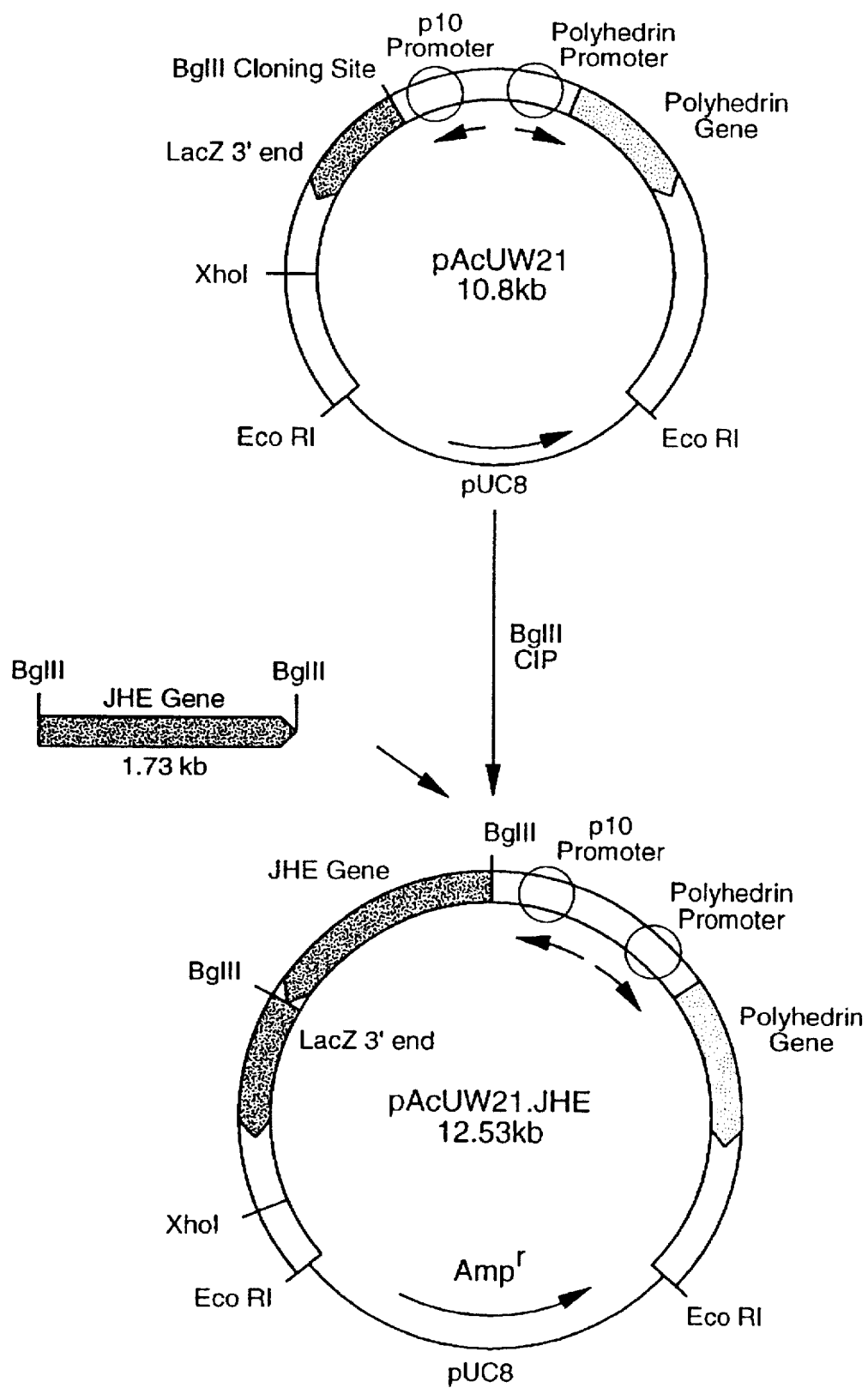
FIG._2

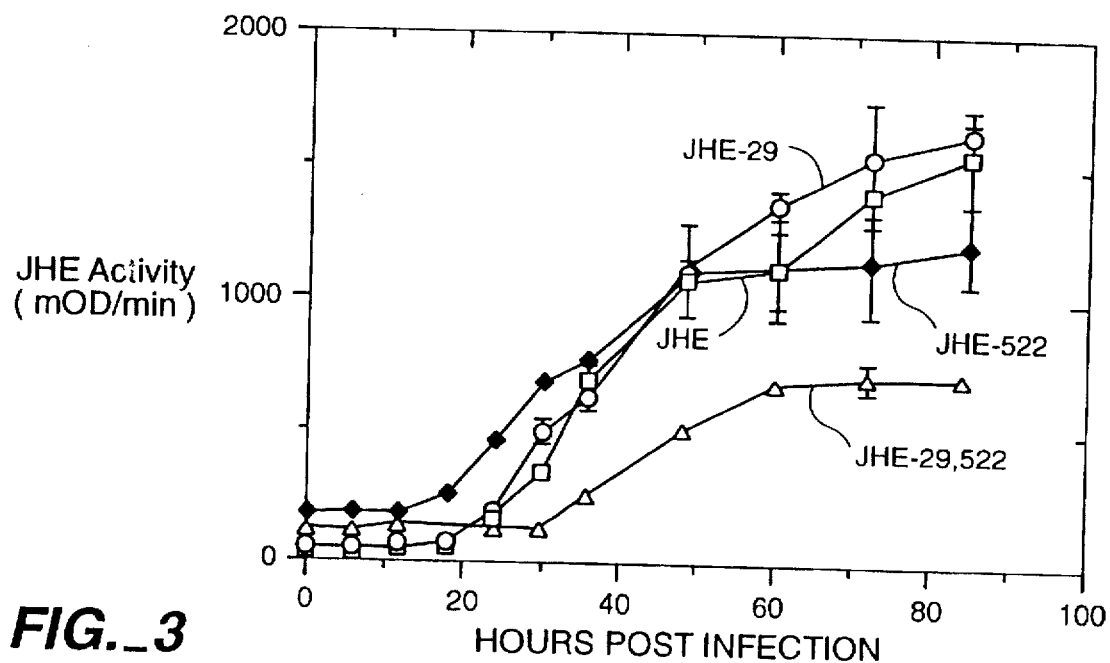
FIG._3
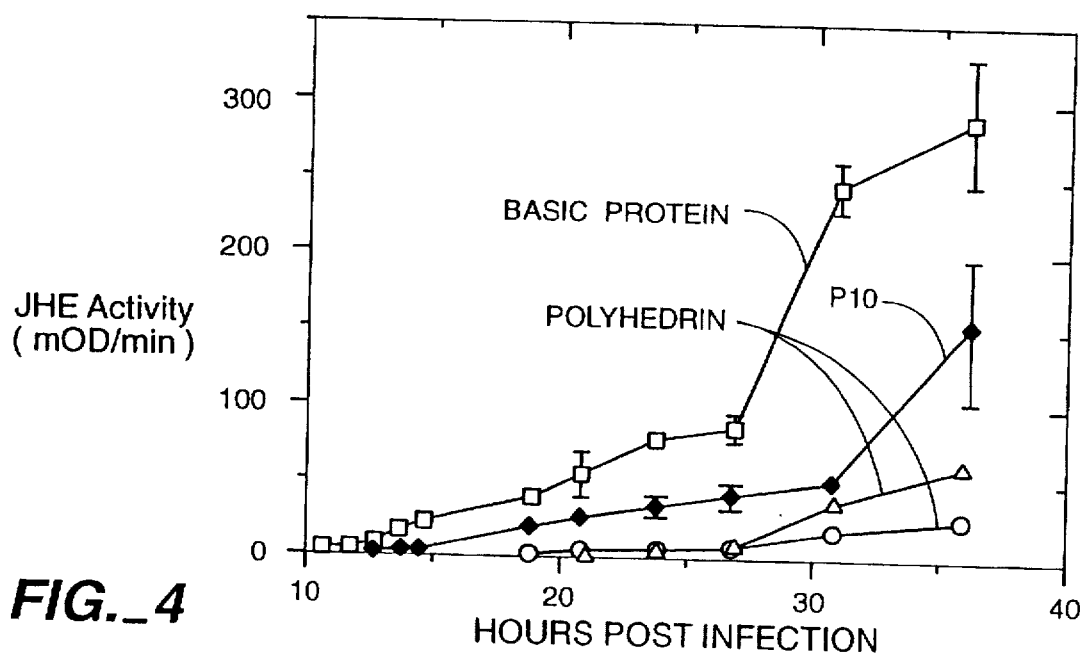
FIG._4

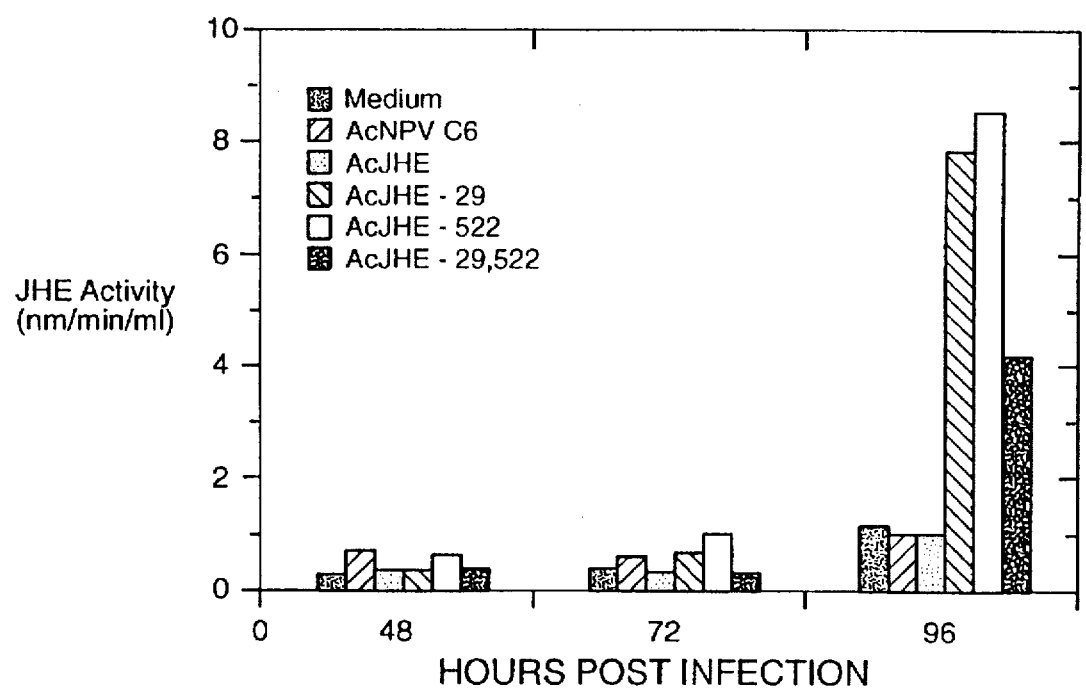
FIG._5

VIRAL VECTOR CODING FOR JUVENILE HORMONE ESTERASE

This is a division of application Ser. No. 07/927,851, filed Aug. 10, 1992 U.S. Pat. No. 5,643,776, which is a continuation-in part of U.S. Ser. No. 07/725,226, filed Jun. 26, 1991, now abandoned, which was a continuation of Ser. No. 07,265,507, filed Nov. 1, 1988, now abandoned.

This invention was made with Government support under NIH Grant No. ES-02710, NSF Grant No. DCB-85-18697 and USDA Grant No. 85-CRCR-1-1715.

FIELD OF THE INVENTION

The present invention relates to uses of nucleotide sequences coding for juvenile hormone esterase, and more particularly to recombinant expression vectors including juvenile hormone esterase or mutant coding sequences having uses such as in controlling insects.

BACKGROUND OF THE INVENTION

The lepidopteran family noctuidae includes some of the most destructive agricultural pests, such as the genera Heliothis, Helicoverpa, Spodoptera and Trichoplusia. For example, included in this family are the tobacco budworm (*Heliothis virescens*), the cotton leafworm (*Alabama argillacea*), the spotted cutworm (*Amathes c-nigrum*), the glassy cutworm (*Crymodes devastator*), the bronzed cutworm (*Nephelodes emmedonia*), the fall armyworm (*Laphygma frugiperda*), the beet armyworm (*Spodoptera exigua*) and the variegated cutworm (*Peridroma saucia*). Juvenile hormone esterase is responsible for the stage-specific metabolism of juvenile hormone in such insects.

Juvenile hormone and juvenile hormone esterase have been studied extensively in the Lepidoptera. In the final larval growing stage of these insects, there is a rapid decline in the juvenile hormone titer which initiates the physiological and behavioral events preceding pupation and adult development. This decline in the juvenile hormone titer appears to be regulated by an increase in degradation by juvenile hormone esterase as well as a reduction of biosynthesis. Juvenile hormone esterase activity is very low in the early stadia of larval growth. Even at the peak activity levels in the blood of the final stadium, the concentration of juvenile hormone esterase has been estimated at less than 0.1 percent of the total protein. Yet the enzyme has a high affinity for juvenile hormone.

The initial reduction in juvenile hormone titer in the last larval stadium initiates a sequence of events leading to pupation. Powerful and selective chemical inhibitors of juvenile hormone esterase have been used in vivo to demonstrate the developmental consequences of blocking the activity of juvenile hormone esterase. For example, a group of the chemical inhibitors of juvenile hormone esterase are the trifluoromethylketone sulfides, as described by U.S. Pat. No. 4,562,292, issued Dec. 31, 1985, inventors Hammock et al. Treatment in the final larval stadium of the tomato hornworm (*Manduca sexta*) and other moth larvae with potent inhibitors can block almost all of the blood juvenile hormone esterase activity and cause a delay in the time of metamorphosis, presumably by allowing juvenile hormone to remain present.

Classical methods of protein purification have been inefficient for the large-scale purification of juvenile hormone esterase because the esterase is in picomole amounts even at its peak levels. More recently, a purification method for juvenile hormone esterase from larval blood has been developed. Abdel-Aal and Hammock, *Science*, 233, pp. 1073–1076 (1986).

There is a need for genes which when produced in expression systems will lead to rapid insect death, disruption of development, and/or cessation of feeding. Recent efforts have centered on the insect specific toxins from *Bacillus thuringiensis* (Merryweather et al., 1990), from the scorpions *Buthus eupeus* (Carbonell et al., 1988) and *Androctonus australis* (Stewart et al., 1991; McCutchen et al., 1991; Maeda et al., 1991) and from the mite *Pyemotes tritici* (Tomalski and Miller, 1991).

SUMMARY OF THE INVENTION

It is one object of the present invention to provide a recombinant expression vector that halts feeding and disrupts the development of insect pests by artificial expression of juvenile hormone esterase at an early stage of development.

One aspect of the present invention comprises a vector with a coding sequence capable of expressing a protein in a host cell expression system. When expressed, the protein degrades, binds with or sequesters juvenile hormone or a juvenile hormone homolog within the host.

A preferred use of the inventive vectors is for expression in insects by infecting susceptible host insect cells with a recombinant baculovirus so that insect development is disrupted. Improved expression of JHE in a baculovirus system (with an improved lethal dose value) has been provided by mutagenesis. This improved expression is important because excessive insect feeding (before the virus acts on the insect pest) can result in unacceptable crop damage. Our improved vectors achieve earlier insect kill.

In another aspect of the present invention a transgenic, non-human organism has a nucleotide sequence introduced therein. The nucleotide sequence preferably is substantially similar to the cDNA illustrated by SEQ ID NOS:1 or 2 or to the gene illustrated by FIG. 6. These sequences are effective to alter at least one determinable property of the organism when expressed. A preferred altered property is enhanced degradation of a methyl ester containing compound, such as disruption of juvenile hormone expression.

In another aspect of the present invention, the recombinant expression vectors capable of expression in a host insect or plant cell include coding sequences for a mutant or chimeric protein of a juvenile hormone esterase and a promoter that is heterologous with the coding sequence.

These and other aspects and advantages of the present invention will now be more fully described.

BRIEF DESCRIPTION OF THE DRAWINGS

FIG. 1 illustrates a restriction map for a cDNA coding for juvenile hormone esterase;

FIG. 2 illustrates construction of a plasmid embodiment in accordance with the invention (designated pAcUW21.JHE);

FIG. 3 graphically illustrates the expression of wild type and three modified JHEs, which are inventive embodiments, in baculovirus infected Sf cells in vitro;

FIG. 4 graphically illustrates the expression of JHE in the system used for the FIG. 3 data (baculovirus infected Sf cells in vitro), but with three different promoters as additional inventive embodiments;

FIG. 5 graphically illustrates the in vivo expression of wild type and several modified JHEs post-injection of recombinant baculoviruses into second instar *Manduca sexta*; and FIG. 6 summarizes the JHE gene itself.

DETAILED DESCRIPTION OF THE PREFERRED EMBODIMENTS

The lepidopteran family Noctuidae includes a number of economically destructive agricultural pests. Briefly, two epithelial hormones control metamorphosis in such insects. Asteroid hormone, 20-hydroxyecdysone, causes the molt, while a terpenoid hormone, juvenile hormone (JH), determines the nature of the molt. If juvenile hormone titers are high, then the molt is isometric to a larger larval stage. If juvenile hormone titers are low, then anisometric molt to a pupal stage will occur. Thus, the initial reduction in juvenile hormone titer in the last larval stadium is a key event in insect development in that it initiates a sequence of events leading to pupation and early in this sequence of events is the cessation of feeding. This reduction in juvenile hormone titer is accomplished by a reduction of biosynthesis and a tremendous increase in the highly aggressive enzyme known as juvenile hormone esterase (JHE).

Juvenile hormone esterase (JHE) is biochemically interesting in that it is an extraordinarily efficient enzyme. The very low $K_m$ $6\times10^{-8}$M of juvenile hormone esterase, its relatively high $k_{CAT}$, and the low molarity of the enzyme even in the last larval stadium indicate that production of even small amounts of juvenile hormone esterase will overpower the ability of the corpora allata to make juvenile hormone (JH). The destruction of the juvenile hormone will be accelerated by the juvenile hormone hemolymph carrier protein. This carrier protects juvenile hormone at earlier stages of development, but it binds juvenile hormone less tightly than the esterase ($K_d$=6.1×10$^{-7}$M for $H.$ $virescens$), and thus serves to accelerate degradation of juvenile hormone by juvenile hormone esterase and keeps juvenile hormone out of lipophilic depots.

Under $V_{max}$ conditions, the juvenile hormone esterase present in a single fifth stadium noctuid larva could hydrolyze over 100,000 times as much juvenile hormone each minute as is present in an entire larva at any time during development. Under physiological conditions, juvenile hormone esterase acts as an infinitely large sink capable of extracting juvenile hormone and other susceptible substrates from lipid depots and carriers by mass action and instantly inactivating it. Thus, precocious appearance of juvenile hormone esterase will reduce juvenile hormone titers, typically resulting in irreversible termination of the feeding stage, attempted pupation and death of the pest insect.

Juvenile hormone esterase is an insect protein which appears at critical times in the insect's life. It appears to present no risk to other groups of organisms. It is nonlethal to an individual cell which allows and perhaps encourages viral replication; yet the enzyme will fatally disrupt the normal development of the organism. Because the substrate (juvenile hormone) readily penetrates membranes, the juvenile hormone esterase need only be expressed in a few cells to deplete juvenile hormone. Differential tissue depletion of juvenile hormone is likely to be even more rapidly fatal to an insect than uniform depletion.

Numerous attempts have been made to purify juvenile hormone seterases, but purification of the low abundance enzyme from a small tissue source has proven very tedious. U.S. Pat. No. 5,098,706, issued Mar. 24, 1992, and filed concurrently with Ser. No. 07/265,507 of which this is a continuation-in-part, incorporated by reference, exemplifies the administration of an affinity purified enzyme to insects which results in anti-juvenile hormone activity. Such anti-juvenile hormone activity is effectively lethal, for example in blocking damage by herbivorous insects.

One aspect of the present invention concerns uses of the coding sequence for juvenile hormone esterase. SEQ ID NO:1 sets out the coding sequence for one cDNA of JHE, and SEQ ID NO:2 sets out the coding sequence for another. These coding sequences are for juvenile hormone esterase from *Heliothis virescens*, although there is homology to *Helicoverpa zea* (formerly *Heliothis zea*), to *Tricoplusia ni* and (at lower stringency) hybridization to *Manduca sexta*. Further, JHE isolated (or derived) from *Heliothis* (*Helicoverpa*) *viresens* functions to hydrolyze every known form of JH. This means that a coding sequence for JHE derived from *H. virescens* can be used to isolate the gene or the message from a variety of species. FIG. 6 illustrates the JHE gene for *H. virescens* and gives, among other things, restriction enzyme sites.

The pattern of JHE activity and low message abundance suggests that expression of the enzyme is tightly regulated, perhaps at the level of transcription. In Lepidoptera, the structure and transcriptional control of developmentally regulated genes has been investigated, but most of these genes are multiple copy and the mRNA is abundant. By contrast, JHE from *H. virescens* apparently is encoded by the single gene illustrated by FIG. 6, which produces a low-abundance message.

JHE Coding Sequence Cloning

As will also be described in Examples 1 and 2, the clone containing the sequence of the mRNA transcript of juvenile hormone esterase from *Heliothis virescens* was isolated from a lambda gt-11 expression library. To make the expression library, total RNA was isolated by homogenizing fat bodies in guanidinium thiocyanate and centrifugation through cesium chloride. The fat bodies were from last instar larvae that had been treated with epofenonane 24 hours previously. Poly-adenylated RNA was prepared by one cycle of oligo-dT chromatography from which cDNA was synthesized and size selected for greater than 1350 base pairs. The size selected cDNA was suitably processed and ligated to arms of a lambda-gt11 phage expression vector. The ligated DNA was then packaged into phage heads, infected into host cells and plated on a lawn of host *E. coli*. The cDNA library was not amplified prior to screening.

Screening was done immunochemically on nitrocellulose filters to which proteins from plated phage had been bound after induction of protein synthesis. Clones reacting with antibodies specific for juvenile hormone esterase were plaque-purified after detection with immunohistochemical means. A second round of screening was then conducted upon the isolated clones with hybridization to a mixture of synthetic nucleotides complementary to the deduced mRNA sequence possibilities determined from the N-terminal amino-acid sequence of juvenile hormone esterase.

The amino acid sequence was determined by automated Edman degradation of the purified protein. From this round of screening, three 3,000 basepair clones, 3hv1, 3hv16 and 3hv21 were isolated, subcloned into plasmids and subjected to restriction analysis. The later two clones have their sequences given by SEQ ID NOS. 2 and 1. Their length matched the 3,000 basepair length of the juvenile hormone esterase mRNA transcript as determined by Northern blotting with radiolabeled DNA of clone 3hv21. An 840 basepair fragment of the 5' coding region of 3hv21 was then sequenced. The sequence confirmed the clone to be that coding for juvenile hormone esterase as the deduced amino-acid sequence matched 33 of the 35 of the doubly confirmed amino-acids sequenced at the N-terminus of the purified protein.

Uses of JHE Coding Sequence

The JHE coding sequence, various mutations and analogs and restriction fragments thereof have a variety of uses. For example, the JHE coding sequence is useful in characterizing insects related to or within the Heliothis group. Thus, Example 3 describes the utility of the cDNA as a diagnostic tool. Once the insect has been characterized, in laboratory or field, then appropriate steps for control may be taken.

In addition, the reduction in JH titer in some insects is accomplished by a combination of reduction in biosynthesis and an increase in degradation by JHE. Thus, the JHE coding sequence can be used in combination with an agent that reduces the JHE biosynthesis or influences its distribution and kinetics.

Since the juvenile hormone esterase coding sequence (illustrated by SEQ ID NO:1 and SEQ ID NO:2) has been determined, methods to elicit the precocious expression of juvenile hormone esterase for insect control are now possible.

The recent development of a vital expression vector from a virus endemic in and selective for noctuid species permits practical field control systems for the Boll Worm and other insect pests. U.S. Pat. No. 4,745,051, issued May 17, 1988, inventors, Smith, et al., incorporated herein by reference describes a method for producing a recombinant baculovirus expression vector capable of expression of a selected gene in a host insect cell. The method exemplified by U.S. Pat. No. 4,745,051 was used to express β-Interferon by infecting susceptible host insect cells with a recombinant baculovirus expression vector. Briefly, baculovirus DNA is cleaved to obtain a DNA fragment containing at least a promoter of the baculovirus gene. One baculovirus gene is that coding for polyhedrin, since the polyhedrin protein is one of the most highly expressed eucaryotid genes known, although other promoter and hybrid promoter sequences may be used.

Although the polyhedrin promoter can be used in preparing inventive expression vectors, we have found JHE can be produced even earlier and at still greater levels under the p10 and basic protein promoters, as illustrated by the data of FIG. 4. The preferred baculovirus utilized is *Autographa californica* , although other baculovirus strains may be suitably utilized. *Autographa californica* (AcNPV) is of particular interest as various major pest species within the genera Spodoptera, Trichoplusia, and Heliothis are susceptible to this virus.

In the present invention, a baculovirus may be modified by the method described by U.S. Pat. No. 4,745,051, but by utilizing the juvenile hormone esterase coding sequence (or a mutant of JHE coding sequence) rather than the β-Interferon gene. A recombinant expression vector thus comprises a JHE coding sequence or a JHE mutant under the control of a promoter sequence (such as the polyhedrin, p10 or basic protein promoters), which is heterologous with the JHE coding sequence and which regulates the transcription thereof. Expression of the JHE coding sequence gene is accomplished by infecting susceptible host insect or plant cells so as to produce precociously appearing juvenile hormone esterase. In insect cells the JHE appearance, even at low levels, disrupts insect development. In plant cells the JHE appearance can provide protection against insect predators.

Aspects of the present invention will be illustrated by a number of examples. Examples 1–3 primarily describe work obtaining cDNA for JHE and some characterizations for the JHE gene. Example 4 describes preparation of improved baculovirus (particularly useful as insecticidal agents) by forming mutants of the original JHE nucleotide sequences, and also discusses various other mutations that can be made. Example 5 describes preparation of inventive vector embodiments with several different promoters. Example 6 describes further characterizations of the JHE gene itself.

Preparation of mutants

The degradation of proteins within cells occurs by many pathways, but the best known are the ubiquitin and lysosomal pathways. For degradation by ubiquitin and recognition by many lysosomal enzymes, a protein must either have free lysine (K) residues available on the surface of the protein or appropriate lysine containing sequences respectively. For ubiquitin degradation, appropriate lysines are often found near the N-terminus of the protein. JHE contains a lysine at position 29 and has tryptophan as the N-terminal amino acid, which is a possible susceptible residue for targeting a protein to ubiquitin degradation. In addition, lysine residues occurring in a region rich in proline, glutamate, serine, and threonine are important for both ubiquitin and lysosomal protease recognition. JHE has one such lysine at position 522. These lysines were changed to arginine (R) (K29R and K522R) by site-directed mutagenesis, and then the individual mutants and the combined mutant (K29R+K522R) were tested in the baculovirus system for insecticidal activity.

In addition, an inactive JHE may bind and sequester juvenile hormone rather than degrade it and thus be more effective than active JHE. Thus, natural insect proteins when modified by these methods can have deleterious effects on the insect. A catalytic site mutation of serine 201 to glycine was made (S201G) and tested for insecticidal activity.

The double lysine mutant (sometimes referred to as "KK" and sometimes "29,522" and sometimes as "K29R, K522R") and the catalytic serine mutant (S201G) of recombinant JHE enhance the ability of the AcNPV to kill in both *Heliothis virescens* and *Trichoplusia ni*. The insecticidal activity of the catalytically deficient S201G mutant of JHE is unusual and possibly contradictory to the current theories of JHE action. The times required for 50% death of test insects are similar to those required for scorpion toxins that have recently been reported in the literature, engineered in A.cal NPV, and are a considerably safer alternative. These viruses can be produced easily in both tissue culture and in laboratory or industrial insect colonies, unlike their toxin containing competitors, and represent a minor variation of a protein that occurs naturally in the insects. As this enzyme occurs in all insects, the engineering of this JHE into NPVs with differing host specificity allows a wide spectrum of pests to be controlled in a rapid and effective manner.

In addition to the particular in vitro site-directed mutagenesis technique described by Example 4 to exemplify the mutation aspect of the invention, there are numerous techniques for mutagenesis which may be employed to improve utility. For instance, it is possible to employ other nucleotide-mediated mutagenesis protocols and similar techniques can be used to create deletions or insertions. Deletions or insertions may be systematically incorporated, either by linker-insertion, linker-scan, or nested deletion. For example, it is possible to randomly insert small linkers into the JHE sequence. Other techniques for less structured mutagenesis include the use of degenerate nucleotide pools, misincorporation by DNA polymerases and chemical mutagenesis. Standard restriction and ligation techniques can be used to create large deletions or chimeric enzymes. New PCR methods for mutagenesis could also be used to generate classes of mutations.

Whether by site-directed mutagenesis techniques or other mutagenesis protocols, we consider sequences with significant homology to SEQ ID NO:1 or SEQ ID NO:2 or to the JHE gene itself (illustrated by FIG. 6) to be within the scope of this invention. By "significant similarity or homology" is meant that the nucleotides have greater sequence similarity than by chance alone and that the protein coded by the sequence, when expressed in an appropriate host cell expression system, degrades, binds with, or sequesters juvenile hormone or those endogenous proteins commonly recognized as juvenile hormone homologs due to their structural similarity to JH.

Another way of looking at coding sequences that are substantially the same as a juvenile hormone esterase coding sequence are those where the physiological or biological action is as has just been described and the protein expressed by the coding sequence reacts with a methyl ester containing compound. For example, the JHE of *H. virescens* and that of several other species all have high specificity for JH with a high $k_{CAT}/K_M$ ratio (>$10^8$). Juvenile hormone itself is, of course, a methyl ester containing compound (and includes an epoxide functionality), and of interest her enzymes of interest where expression of the coding sequence leads to enhanced degradation of JH. For example, epoxide hydrolases are known to act similarly to JHE by hydrolysis of JH to yield biologically inactive diols.

Example 4 illustrates use of mutagenesis in baculovirus expressing JHE as an insecticidal agent, which are improved over recombinant baculoviruses expressing JHE, since several mutants have resulted in improved properties (e.g. reducing the lethal dose significantly in *Heliothis virescens*). For example, a double mutant has resulted in lethal dose improvements so that insects are killed about one day or one and one half days faster than kill rates with the wild type virus. This is significant for crop protection because the plant damage done to crops is a function of time that the crops are vulnerable to the insects.

Example 5 illustrates JHE activity, in vitro under the control of several different viral promoters. The expression level of JHE with a basic protein promoter is particularly exciting because greatly increased JHE expression (at levels up to about 5 times higher) have been demonstrated. This is particularly surprising because use of the basic protein promoter with other coding sequences has indicated lowered expression rather than enhanced expression of the protein coded by the coding sequence. We believe the striking difference in expression levels lies in the fact that JHE is a packaged, or secreted, protein. As a consequence, increased expression levels of secreted or exported proteins should be achievable by combining the basic protein promoter with a nucleotide coding sequence coding for the secreted or exported protein. The sequence and composition of the 19 residues prior to the $NH_2$ terminal Trp of the secreted major form of JHE match well with the consensus for other signal peptides for secretion.

Modified, or mutated, JHEs in accordance with the invention are not limited to just the *H. virescens* insect because the JHE enzyme is capable of hydrolyzing all known JH homologs with similar $k_{CAT}/K_m$ ratios, as well as related methyl esters. This means that JHE and JHE mutants are applicable in many expression systems, and it is clear that JHE can convert a wide variety of methyl esters to the corresponding free acids.

The juvenile hormone esterase shows high selectivity for rapid hydrolysis of methyl and thiomethyl esters. This rapid catalytic activity can be used to yield colorimetric assays using substrates such as octanoic acid thiomethyl ester or methyl β-(1-pentylthio)propiothiate, methyl β-(1-pentoxy) propiothioate, and related β and γ homologs resulting in a catalytic marker. The high stability of juvenile hormone esterase and its rapid turnover of thiomethyl esters also makes it an attractive reporter enzyme. The juvenile hormone esterase expressed in a system such as the baculovirus system can lead to the rapid hydrolysis of a variety of methyl and thiomethyl esters. Methyl esters, thiomethylesters, or methylcarbonates can be removed to activate drugs or pesticides such as clofibric acid methyl ester, bifenox, butoxone methyl ester, dacthal, diclofop-methyl, chlorfenprop-methyl, or esters or carbonates of substituted 2,4-dinitrophenyl uncouplers. The catalytic activity also can be used to degrade toxic materials containing a methyl ester such as pesticides in environmental samples or drugs or poisons such as warfarin, heroin, or bisacodyl following overdose.

We believe it likely that the biological activity comes from disrupting a fundamental process in insects that is related to turnover of native proteins. Thus, our mutagenesis technique is applicable to the genes of a variety of species and to proteins extending beyond JHE.

Other Uses and Particular Uses of the JHE gene

There are advantages to using the JHE gene itself (as opposed to using a cDNA for JHE) in some systems. For example, use of the gene is believed preferable in transgenic monocots and transgenic (non-human) mammals, and the expression obtained from use of the gene itself can be higher than with cDNA. Although insect control is the utility we presently contemplate as particularly preferred, the JHE gene should also be expressed in plants, mammalian systems, bacteria, fungi, and algae, in addition to insects and viruses.

For example, when the JHE gene is expressed in plants, then the enzyme should act on ester-containing compounds other than insect juvenile hormone to convey herbicide resistance to the plants or may be used in biosynthetic processes to hydrolyze methyl esters selectively. The catalytic activity can be used to remove methyl ester protecting groups in specialty compound synthesis such as methyl esters of retenoic acid or chrysanthemic acid. The catalytic activity on methyl esters can be used to activate or deactivate biologically active materials with a carboxylic acid blocked by a methyl ester.

Examples of deactivation include compounds such as the sulfonyl urea herbicides metsulfuron-methyl, tribenuron-methyl, sulfometuron-methyl, prisisulfuron, bensulfuron-methyl, or the herbicide DME [2-(diphenylmethoxy)acetic acid methyl ester]. The catalytic activity could be used to hydrolyze methyl esters critical in the biosynthesis of natural products. For instance, a methyl esterase will convert Protoporphyrin IX monomethyl ester to Protoporphryn IX thus reversing the biosynthesis of the key plant pigment chlorophyll.

Expression of the JHE gene may also protect plants from invertebrates other than insects. Expression of the JHE gene by algae may be useful for control of mosquitos or other disease vectors.

Nucleotide sequences of this invention can be introduced into non-human organisms to form transgenic organisms. Introduction of the sequences may be double or single stranded form, and can be "sense" or "anti-sense" (that is, with the sequence reversed with respect to the sequence illustrated such as by SEQ ID NOS:1 or 2 or to the gene illustrated by FIG. 6). Shorter fragments, as small as about 16 sequential bases in length, have various uses, such as in diagnostic applications, with 16 sequential bases believed to be about the minimum length for hybridization. The ready availability of JHE from expression systems of the invention, particularly from bacteria or viruses, should permit other diagnostic applications, such as the use of JHE as a reporter enzyme that can be coupled to antibody.

EXAMPLE 1

Animals

Larvae of *Heliothis virescens* were obtained from a research facility of Dow Chemical Company located at Walnut Creek, Calif.

Materials

Radioactively labeled reagents obtained from Amersham (Arlington Heights, Ill.). Other chemicals were of the highest quality available. Enzymes were obtained from Promega Biotec (Madison, Wis.), Boehringer Mannheim Biochemicals, (Indianapolis, Ind.), United States Biochemical Corporation (Cleveland, Ohio) and Sigma (St. Louis, Mo.).

A Bluescript plasmid with a cDNA insert from *H. virescens*, 3hv1 (sequence not shown), 3hv21 (SEQ ID NO:1), and 3hv16 (SEQ ID NO:2), was isolated from the *E. coli* host cells and host chromosomal DNA using the alkaline lysis miniprep procedure described in Maniatis et al., *Molecular Cloning*, Cold Spring Harbor Laboratory (1982). The N-terminal Bam HI restriction fragment from the above preparation was ligated into phage M13 (mp19). Thus, in a 25 μl volume 0.2 μg of Bam HI cut mp19 was added to 1.0 μg of Bluescript plasmid cut with Bam HI. After the addition of ligase the reaction was allowed to proceed 60 minutes at room temperature and overnight at 4° C.

Ligated DNA was used to transform competent *E. coli* host cells are described in Rodriquez, *Recombinant DNA Techniques: An Introduction*, Addison-Wesley (1983). Either 0.1 μl, 1 μl or 10 μl of the ligation mixture was added to 200 μl of competent JM101. After incubation on ice the mixture was added to soft agarose at 43°–45° C. for 2 minutes. The agarose and cells were plated with X-gal and IPTG, and incubated at 37° C. Recombinant transformants were present as white plaques.

Isolated white plaques were picked and grown for 6 hours at 37° C. in 1×YT medium. Double-stranded DNA was prepared by the method described in Rodriquez, supra. Briefly, the host cells were pelleted and resuspended in a sucrose EDTA buffer. RNAse was added and the cells lysed in 1% SDS with0.2N NaOH. The host chromosome DNA was pelleted by centrifugation and the supernatant with double-stranded RF M13 DNA removed. From the supernatant double-stranded M13 was precipitated in isopropanol and washed with ethanol. The double-stranded M13 was cut with Bam HI and run on a 0.8% agarose gel with Bam HI cut Bluescript plasmid to ensure the subcloned M13 fragment was the same size as the fragment from the original Bluescript plasmid.

The next step was to conduct a C-test for complementary single-stranded DNA from M13 plaques. Identification of both orientations of a cloned insert is useful for single-strand sequencing because it is possible to sequence from both ends toward the middle. Essentially, the transformed host cells (JM101) from independent plaques were grown for 4–6 hours in 1×YT medium. Approximately 8 μl of supernatant from each plaque was removed and supernatant from various combinations of different plaques was mixed with glycerol, salt, and SDS. The mixtures were incubated at 60°–70° C. for 15 minutes and allowed to cool. A sample of the mixture was placed on a 0.8% agarose gel to detect hybridization by retarded migration in the gel.

Single-stranded DNA from M13 with inserts in opposite orientation was then prepared. To do so, transformed cells were grown for 4–6 hours at 37° C. Single-stranded DNA was extruded into the medium and precipitated with PEG and NaCl. After resuspension protein was removed with phenol chloroform. Several volumes of ethanol was added to the aqueous for precipitation. The pellet was washed in 70% ethanol, dried and resuspended in autoclaved water.

Sequencing of the above single-stranded DNA was based on the chain termination method of Sanger et. al, *PNAS*, 74, 5463 (1977). Bam HI fragments in both orientations in M13 were sequenced. For sequencing reactions, $^{32}$P ATP was used with the reagents and instructions supplied in the sequence kit (United States Biochemical). The sequencing reactions were run on 4% and 6% acrylamide gels. Audioradiographs of the gels were read after overnight exposure of the film to dried gel. The complete Bam HI insert of approximately 840 base pairs was read. This included the putative sequence for the secretion signal peptide and the N-terminal coding sequence which corresponded to the N-terminal amino acid sequence for JHE. The identity of the JHE cDNA insert was initially established in this manner.

EXAMPLE 2

Protein Sequencing

Juvenile hormone esterase was purified (as described by Abdel-Aal and Hammock, *Science*, 283, pp. 1073–1076 (1986)) from the hemolymph of last instar larvae of *Heliothis virescens*. The purified preparation was seen to be a single band when analyzed by electrophoresis in the presence of SDS (Laemmli, Nature, 227, pp. 680–685 (1970)) and isoelectric focusing on a polyacrylamide gel having a ph 4.0 to pH 6.5 gradient (Pharmacia, Piscataway, N.J.). However, when subjected to Edman degradation, two proteins were indicated to be in the preparation. The presence of isoforms of JH esterase in *H. virescens* is consistent with observations of the enzyme in other insects. From the major form was obtained a readable sequence of 35 residues. The signal from the minor form indicated a protein having a two residue extension of Ser-Ala followed by a sequence of five residues identical to the ultimate five residues at the N-terminus of the major form. Amino acid sequencing at the N-terminal of juvenile hormone esterase was done with a Beckman 890M liquid phase sequencer.

Probe Preparation

Both antibodies against juvenile hormone esterase and nucleotides complementary to the juvenile hormone esterase message were used as probes to detect recombinant clones coding for juvenile hormone esterase. Antisera to juvenile hormone esterase was prepared with New Zealand White female rabbits (Vaitukaitis, *Methods in Enzymology* (Langone and Yon Vunakis, eds.) 73, pp. 46–52, Academic Press, New York (1981)). To reduce background, the antisera was incubated overnight at 4° C. with diluted *Heliothis virescens* hemolymph devoid of juvenile hormone esterase activity (the antisera was diluted 1:10 in a solution of 10 mg/ml hemolymph protein in pH 7.4, I=0.2 phosphate buffer containing 0.01% phenyl thiourea). A final dilution of 1:750 was used for screening. A mixture of 32 14-mer nucleotides were synthesized using a Syntec model 1450 synthesizer. Their sequences were complementary to all the possibilities of the mRNA structure deduced from the amino acid sequence of the N-terminal. The nucleotides were purified on a Nensorb 20 nucleic acid purification cartridge (Dupont Co., Wilmington, Del.) and end-labeled with $^{32}$P with T4 polynucleotide kinase and [$^{32}$P]ATP (>6000 Ci/mmol) by a standard technique (Zeff and Geliebter, *BRL Focus* 9-2, pp. 1–2 (1987)).

cDNA Synthesis and Cloning

Total RNA was isolated by homogenizing fat bodies in guanidinium thiocyanate and centrifugation through cesium chloride (Turpen and Griffith, *BioTechniques* 4(1), pp. 11–15 (1986)). The fat bodies were dissected from last instar larvae that had been treated with epofenonane 24 hours previously to increase the level of Juvenile hormone esterase activity (Hanzlik and Hammock, *J. Biol. Chem.*, 262, pp. 13584–13591 (1987)). At the time of treatment, the larvae weighed 200–300 mg. Polyadenylated RNA was prepared by one cycle of oligo-dT chromatography (Aviv and Leder, *Proc. Nat. Acad. Sci. USA*, 69, pp. 1408–1412 (1972)) using oligo-dT cellulose (Collaborative Research, Cambridge, Mass.). Synthesis of cDNA from 2 μg of poly-A RNA was done by the method of Gubler and Hoffman (Gubler and Hoffman, *Gene*, 25, pp. 263–269 (1983)) with a cDNA kit (Amersham) and a variation of its protocol. The protocol was varied in the priming of the first strand synthesis wherein 100 ng of random hexamer primers (Pharmacia) were added 30 minutes after initiation of first strand synthesis by oligo-dT primers done according to the protocol. Size selection of the cDNA for >1350 basepairs was done with gel permeation using a spin column (5 Prime-3 Prime, Paoli, Pa.). The size selected cDNA was treated with Eco R1 methylase, ligated to Eco R1 linkers and treated with Eco R1 restriction endonuclease according to the protocols presented by Huynh et al. (Huynh, Young and Davis, *DNA Cloning: A Practical Approach* (Glover, D. M., ed.), pp. 49–78, IRL Press, Oxford (1984)). The free linkers were removed by three cycles of ultrafiltration using Centricon 30 microfiltrators (Amicon, Danvers, Mass.). The cDNA was then ligated to arms of a lambda gt11 expression vector derivative (lambda-ZAP, Stratagene Cloning Systems, La Jolla, Calif.) according to the manufacturer's recommendations. The ligated DNA was then packaged into phage heads using a two extract system (Gigapack Gold, Stratagene Cloning Systems), and plated on to rec *E. coli* host cells (XL1-Blue, Stratagene Cloning Systems). Greater than 99% of the clones were recombinant. The cDNA library was not amplified prior to screening.

Screening

Initial screening was done immunochemically on nitrocellulose filters to which proteins from plated phage had been bound after induction of protein synthesis. Clones reacting with antibodies specific for juvenile hormone esterase were plaque-purified after detection with immunohistochemical means (9) using a kit (Protoblot, Promega). A second round of screening was then conducted upon plaque lifts of the isolated clones by hybridization to the mixture of 14-mer nucleotides. This was done by incubating the filters with the labeled oligomers at 35° C. in 5× SSPE, 3× Denhardt's solution, 100 μg/ml low molecular weight DNA after prehybridizing in the same solution sans the oligomers. Washing was done three times at the hybridizing temperature in a solution consisting of 2× SSC and 0.1% SDS. Positively reacting clones were then subcloned into the Bluescript SK M13- plasmid (Stratagene Cloning Systems) by the automatic excision process allowed by the lambda-ZAP vector.

Sequencing

Sequencing of the remaining cDNA insert, and to confirm the 840 base pair sequence, was done with the dideoxy chain termination method (Sanger, Nicklen and Coulson, *Proc. Natl. Acad. Sci. USA*, 74, pp. 5463–5467 (1977)) using modified T7 DNA polymerase (Sequenase, United States Biochemical Corp.) and 35S labeled dATP. Templates were generated by using both denature plasmids (Toneguzzo, Glynn, Levi, Mjolsness, and Hayday, *BioTechniques*, 6, pp. 460–469 (1988)) and single stranded DNA from M13phage (Yanisch-Perron, Vieira, and Messing, *Gene*, 33, pp. 103–119). A rec A- *E. coli* strain (JM109) was used for the amplification of the subclones that were constructed with both restriction fragments and nested deletions (Henikoff, *Gene*, 28, pp. 351–359 (1984)) (kit from Stratagene Cloning Systems). Computer assisted sequence analysis was done with programs written by Pustell (Pustell and Kafatos, *Nucleic Acids Res.*, 12, (1984)).

Additional Library and Sequence Analysis

We decided to construct another cDNA expression library using both random and oligo-dT priming of the first strand. In addition we used cDNA selected for a size greater than 1350 bp for ligation to the vector. Screening 40,000 clones of this library produced 25 immunoreactive clones, five of which hybridized to the nucleotide probes. Three of these clones, designated 3hv1, 3hv16 and 3hv21, were subcloned into plasmids and characterized. All three clones contained 3000 bp inserts that had identical restriction patterns when incubated with Eco RI, Xho I and Bam HI. When the clone, 3hv21, was used as a probe on a Northern blot, it hybridized at low stringency to a single band with a 3.0 kb length.

The amount of screening required to isolate positive clones indicates that the frequency of the JH esterase message during the period of its secretion into the hemolymph during the last instar is relatively low.

We considered the three clones (3hv1, 3hv21, and 3hv16) to be identical due to their identical length and restriction patterns, although slight differences exist as discussed hereinafter. The sequence of clone 3hv21 is shown by SEQ ID NO:1 (was set out by FIG. 2 of Ser. No. 07/725,226 and Ser. No. 07/265,507 of which this is a continuation-in-part and published in the *Journal of Biological Chemistry*, 264:21, pp. 12419–12425 (1989). FIG. 1 shows a restriction map for this clone. The clone was sequenced 100% in both directions. The other clone 3hv16 (SEQ ID NO:2) was used for baculovirus expression, mutagenesis, and bioassays.

SEQ ID NO:1 shows the cDNA sequence of JH esterase, which is a 2989 bp cDNA clone and is nearly a full length copy of the mRNA transcript. There is a short 19 base sequence prior (5') to the first ATG. The position and composition of the bases immediately prior to the first ATG matches the consensus for an insect ribosome binding site except at position −3 where a G (the second most frequent base at this site) replaces an A. After the first ATG, there is a 1714 bp open reading frame followed by an untranslated 1256 bp region including a 12 base poly(A) tail. Translation of the open reading frame predicts a 563 residue protein. The sequence and composition of the 19 residues prior to the N-terminal Trp of the secreted major form of JH esterase match well with the consensus for signal peptides for secretion. The molecular weight of the mature protein (sans signal peptide) is predicted to be 61,012 Da, which is in agreement with the $M_r$ of 62,000 derived from electrophoresis. The sequences of the ultimate 35 amino acids derived from Edman degradation of the major form of JH esterase and that predicted by the cDNA sequence match except at two sites. The residues Val 10 and Phe 33 predicted by the sequence of clone 3hv21 are indicted to be Leu and Pro, respectively, on the sequenced protein (Table 1).

TABLE 1

Amino acid sequence analysis of the N-terminus of JH esterase from *H. virescens*[1]

| Cycle | Residue(s)[2] | Yield[3] |
|---|---|---|
| 1 | Trp (Ser) | 1120 (230) |
| 2 | Gln (Ala) | 780 (360) |
| 3 | Glu (Trp) | 870 (340) |
| 4 | Thr (Gln) | 100 (320) |
| 5 | Asn (Glu) | 800 (350) |
| 6 | Ser (Thr) | 560 (10) |
| 7 | Arg (Asn) | 400 (390) |
| 8 | Ser | 610 |
| 9 | Val | 740 |
| 10 | Leu | 550 |
| 11 | Ala | 340 |
| 12 | His | 380 |
| 13 | Leu | 580 |
| 14 | Asp | 590 |
| 15 | Ser | 460 |
| 16 | Gly | 360 |
| 17 | Ile | 290 |
| 18 | Ile | 390 |
| 19 | Arg | 290 |
| 20 | Gly | 360 |
| 21 | Val | 300 |
| 22 | Pro | 110 |
| 23 | arg | — |
| 24 | Ser | 130 |
| 25 | Ala | 250 |
| 26 | Asp | 190 |
| 27 | arg | — |
| 28 | ile | — |
| 29 | Lys | 170 |
| 30 | phe | — |
| 31 | Ala | 130 |
| 32 | ser | — |
| 33 | Pro | 140 |
| 34 | — | — |
| 35 | gly | — |

[1]Affinity purified JH esterase was subjected to automated Edman degradation on a Beckman model 890M liquid phase sequencer. Derivatized residues were confirmed with two HPLC systems employing reverse phase- and cyano-columns. The amount of protein analyzed was 3 nmol as calculated by Coomasie Blue dye binding.
[2]The initial cycles had strong secondary signals, the identity of which are shown in parenthesis. Residues are capitalized where the identity of the PTH-amino acids were confirmed twice by elution from the two different HPLC systems and are lower case where the identify was assigned on the basis of elution from only one HPLC system.
[3]Yield of secondary PTH-amino acids are shown in parenthesis. Hyphens denote where the yield was not calculated for residues identified on the basis of elution from only one HPLC system.

In addition, the serine present at the N-terminal of the minor form of JH esterase protein that was sequenced is indicated to be Leu −2 on the cDNA. To answer the question of whether the differences were due to the cloning process or were genuine, we sequenced the 5' region of the two other clones, 3hv1 and 3hv16, which were isolated from the same unamplified library as 3hv21.

We found slight differences among all three clones. The sequence of clone 3hv1 translates identically in the N-terminal region as clone 3hv21, but differs at base 94, which is the last position of a code for serine 6. Clone 3hv16 differs at two bases (50 and 104) from clone 3hv21 in the area coding for the N-terminal, one of which causes a substitution of a phenylalanine for leucine 9 and a leucine for valine 10. The substitution of isoleucine for valine at residue position 10 makes the translation of clone 3hv16 match in 34 of 35 amino acid residues determined from the purified protein.

The previous data indicated at least five slightly different translations of genes for JH esterase, which suggests multiple genes or alleles for JH esterase exist in populations of *H. virescens*. Perhaps contributing to the heterogeneity between the cDNA's and protein sequences is the fact that the protein and RNA were extracted from two different colonies of *H. virescens* and represents natural variation.

There are three consensus poly(A) signal sequences (AATAAA) that start at bases 2299, 2315 and 2951. The presence of three signals for polyadenylation may signify alternative processing of the transcript in the 3' region. Strong evidence from studies of another noctuid moth shows that there is a constitutively expressed intracellular form of JH esterase throughout its larval stage and thus the larval stage of *H. virescens*. Thus a means of producing an intracellular as well as a secreted form of JH esterase is indicated to exist.

The protein translated from the cDNA clone contains four asparagine residues, Asn 62, Asn 161, Asn 383 and Asn 496, which are candidates for glycosylation. However, preliminary evidence indicates that should this modification be present on the secreted JH esterase from *H. viresens*, mannose and derivatives of glucose are not present. This information indicates that portions of the JHE sequence can be used to make chimeric esterases of altered properties.

Computer analysis of JH esterase sequence

Comparison of the translation of clone 3hv21 to protein sequences in the protein data bank of the National Biomedical Research Foundation and to translations of proteins characterized as esterases, lipases and serine hydrolases in GenBank revealed homologies to five proteins. Identical residue matches (gaps were counted as one substitution regardless of length) of 24.2%, 23.8%, 23.2% and 23.2%, respectively, were noted to human pseudocholine esterase, *Drosophila melanogaster* acetylcholine esterase, electric ray acetylcholine esterase, and *Drosophila melanogaster* esterase −6. In addition, homology to a region situated toward the carboxyl terminal of the large thyroid hormone precursor, bovine thyroglobulin was noted.

EXAMPLE 3

*Heliothis virescens* and *Heliothis zea* are major pest species which are difficult to identify by visual inspection at the larval stage, yet each species is most readily controlled by different insecticides. A molecular probe for *H. virescens* juvenile hormone esterase was used to identify the larval form of one species from the other.

The N-terminal 800 base pair Bam HI fragment from cloned *H. virescens* JHE was labelled with $^{32}$P and hybridized to genomic DNA from *H. virescens* and *H. zea*. The DNA had been cut with the restriction enzyme Xba I, the fragments separated on a 0.8% agarose gel and transferred to a nylon membrane for hybridization with the probe at 65° C. Autoradiographs of the hybridized and washed filter showed that *H. virescens* has at least 6 bands which are approximately 2.9, 3.4, 4.0, 4.3 6.1, 7.6 and 50 kilobases. By contrast, *H. zea* showed none of these bands, but has two diagnostic fragments at 2.0 and 1.5 kilobases. Thus, the JHE probe was useful as a diagnostic tool.

EXAMPLE 4

Plasmids described below are named with a"p" followed by a code indicating their origin, and after a period the gene that they code for. Viruses are named in a similar fashion with Ac indicating that they were derived from the mNPV (multiple nuclear polyhedrosis virus) of the moth *Autographa californica*.

Site-directed mutagenesis

The cDNA coding sequence for JHE from clone 3hv16B (SEQ ID NO:2) was selected for mutagenesis. This JHE clone is in the plasmid vector pBluescriptSK+ (Stratagene) and prior to commencement of the mutagenesis reactions, the JHE coding region was removed by digestion with the restriction endonuclease BglII and recloned into the same vector to obtain the reverse orientation of the insert in the vector. This allowed rescue of the appropriate sense strand for site-directed mutagenesis and also enabled the removal of the JHE coding region By both EcoRI and BglII restriction endonucleases.

Rescue of the single strand DNA for mutagenesis was carried out by standard techniques using the mutant M13 bacteriophage M13K07. Briefly, the JHE clone was grown in E. coli strain XL1-blue in 1 ml of LB medium containing 50 µg/ml ampicillin. At early log phase, 50 µl of culture was added to 100 µl of M13K07 (3×108 pfu/ml) and incubated at 37° C. for 1 hour then 40 µl was transferred to 20 ml of LBpmedia containing 50 µg/ml ampicillin and 50 µg/ml kanamycin. The culture was incubated overnight at 37° C. and ssDNA purified from the culture supernatant as follows. The culture was centrifuged at 2,000 g for 10 minutes then the supernatant was harvested in 16 800 µl aliquots in 1.5 ml Eppendorf tubes and 200 µl of 2.5M NaCl/20% PEG added to each aliquot. After 15 minutes at room temperature, the samples were centrifuged at 16,000 g for 5 minutes and the supernatant removed. The samples were the recentrifuged for 30 seconds and residual supernatant removed. The pellets were resuspended in 100 µl TE (10 mM Tris HCl pH 8/0.1 mM EDTA) per 4 tubes and each of the 4 aliquots was extracted once with buffer saturated phenol and twice with chloroform then precipitated with ethanol. The purified ssDNA was resuspended in a final volume of 50 µl of TE.

The site-directed mutagenesis reactions were carried out by the method of Kunkel et al. (1985) using mutant nucleotide sequences complementary to the "rescued" coding strand obtained from the pBluescript Phagemid. We selected the sites for mutagenesis as follows. One desired mutation was lysine (29) to arginine because this is a lysine located near the N-terminus of JHE. Another desired mutation was lysine (522) to arginine because this is a lysine located within a potential "PEST" sequence and local enrichment of Pro, Ser, Glu, and Thr. A third desired mutation was serine (201) to glycine because conserved catalytic serine motif of Gly X Ser$_{201}$ X Gly.

However, numerous options exist for modification of the JHE cDNA, or gene, to increase insecticidal activity or modify the catalytic functions of the enzyme. For example, it is possible to add or to remove glycosylation sites or to modify the pattern of glycosylation. For many of the site-directed changes it is possible to add, as well as remove, regions of the enzyme that confer defined functions. Other site-directed changes can include alteration of sites resulting in lability to proteases (intra- or extracellular), lysosome recognition sites, tissue (i.e., gut or pericardial) recognition sites, or additional sites involved with ubiquitination. Sites that affect secretion or subcellular targeting can also be modified. Endogenous modification of the enzyme, for example acylation or phosphorylation, can be a goal of mutagenesis. Larger-scale modifications of the enzyme are also possible. For instance, C-terminal trucated forms of JHE have already been shown to retain catalytic activity.

Generation of chimeric proteins is another possibility. One could make chimeric proteins with added peptides to provide dual catalytic activity, increase production in an expression system, and/or change pharmacokinetic properties in a target organism. Thus it may be useful to make a JHE/β-galactosidase enzyme or a JHE/acetyl cholinesterase enzyme. Since X-ray analysis of esterases indicates that they exist in a C-terminal and N-terminal domain it is straightforward to make chimera of various esterases to alter substrate specificity, kinetic properties, or pharmacokinetic properties.

The cDNA or gene may be altered to change mRNA dynamics, rate of transcription, or rate of translation. As will be further described hereinafter, we have also used several different promoters with the JHE coding sequence.

Of the several separate mutations described to illustrate this aspect of the invention, one we designated K29R (lysine 29 mutated to arginine), one as K522R (lysine 522 mutated to arginine), and one as S201G (serine 201 mutated to glycine). All mutations were confirmed by double-stranded sequencing using a sequenase kit (USB).

The K29R, K522R, and S201G JHE mutants were transferred directly to the baculovirus transfer vector pAcUW21 (FIG. 2) by digestion with BglII, gel purification of the JHE coding region, and cloning into the BglII site of the baculovirus transfer vector pAcUW21. A double mutant of JHE (K29R, K522R) was constructed by removal of the N-terminal half of JHE (containing lysine 29) from the pAcUW21.JHE-K522R construct and replacing this with the N-terminal half of JHE from the pAcUW21.JHE-K29R construct. This was done by digesting pAcUW21.JHE-K522R with BamHI which cuts the clone at position 851 in JHE and also cuts the pAcUW21 vector within the polyhedrin gene. This region was then replaced with the equivalent region from pAcUW21.JHE-K29R to regenerate the same vector and clone but containing the K29R mutation. The correct orientation of the modified JHE sequence was confirmed in each case by restriction analysis. Transformation, plasmid preparation and digestions were carried out using standard techniques (Maniatis et al., 1990). The presence of the K29R and K522R mutations were confirmed by digestion with restriction endonucleases. The presence of the S201G mutation was confirmed by sequencing.

Virus Constructs

The viruses AcUW21.JHE-K29R, AcUW21.JHE.K522R, AcUW21.JHE-K29R,K522R and AcUW21.JHE-S201G (henceforth referred to as AcJHE-29, AcJHE-522, AcJHE-29,522 and AcJHE-201 respectively) were made by cotransfection of cell line IPLB Sf-21 of *Spodoptera frugiperda* with polyhedron negative *Autographa californica* nuclear polyhedrosis virus (AcNPV) DNA with the respective plasmids with DNA purified from the polyhedrin negative virus AcRP8 (Matsuura et al., 1987) using Lipofectin Gibco. Homologous recombination between the recombinant plasmids and the vital DNA resulted in polyhedrin positive recombinant viruses against a background of polyhedrin negative non-recombinant virus. Additional cell lines and types of media can be used to alter the production of JHE in vitro.

Virus Purification

Recombinant polyhedrin positive viruses were purified to homogeneity by sequential plaque assays using standard assay procedures. The expression of JHE by recombinant viruses was confirmed by JHE activity and SDS-PAGE for the JHE-29,522 mutant and by SDS-PAGE and Western blotting for the JHE-201 mutant.

Propagation of viruses was carried out in *Spodoptera frugiperda* cells (Sf) IPLB Sf-21 (Vaughn et al., 1977) in ExCell 400 medium (JRH BioSciences) containing 1% Penicillin-Streptomycin (typically containing 100 µg/ml penicillin G and 100 µg/ml streptomycin), at 28° C. Plaque assays were carried out as described by Brown and Faulkner (1977). Purified virus was amplified by larval infection of *Heliothis virescens*. Virus was purified from cadavers by homogenization in double deionized water and differential centrifugation at 4° C. Virus was stored at 4° C. in 0.02% sodium azide. Azide was removed by washing before use of virus in bioassays.

The recombinant virus AcUW2(B).JHE (henceforth referred to as AcJHE), engineered to express the unmodified JHE, and the wild type non-engineered virus AcNPV C6 were also used for comparative purposes.

Baculovirus expression of JHE in vitro

Petri dishes of Sf-21 cells were set up at 1.5×10⁶ cells/ml at 28° C., and infected 24 hours later with AcJHE, AcJHE-29, AcJHE-522 or AcJHE-29,522 at 10 pfu/cell. Expression levels of the modified JHEs attained in vitro in Sf cells were monitored at 6 to 12 hour intervals by colorimetric assay for JHE activity (McCutchen, unpublished), for each modified JHE.

Kinetic parameters (Km and Vmax) were determined for JHE-29,522 using tritiated JH III, or $C_6H_{13}OCH_2C(O)SCH_3$ as substrate, to ensure that these were not altered by the modifications of the JHE coding sequence. Kinetic parameters had been determined previously for JHE, JHE-29 and JHE-522. Crude medium containing baculovirus expressed enzyme was used for these studies.

Bioassay

Second instar larvae of *Trichoplusia ni* or *H. virescens* were infected at various doses of test or control virus to determine the lethal dose. Diet plugs of uniform size (made with a Pasteur pipette) were inoculated with polyhedra (five doses of between 120 to 7 polyhedrin inclusion bodies). Mid-second instar larvae were allowed to feed on the treated diet plugs in 96 well microtitre plates for 24 hours, 50 larvae being infected per dose of virus. After 24 hours, those that had completely consumed the diet plug and therefore ingested the required dose, were transferred to individual tubs of diet and maintained at 24° C. for *T. ni* and 27° C. for *H. virescens*. Controls were mock infected. AcNPV C6 was used as a reference virus for comparison with previous bioassay data for other engineered viruses where the same reference virus was used for reference (McCutchen et al., 1991; Stewart et al., 1991; Merryweather et al., 1990). Mortality was scored after 9 days. Bioassays were replicated 3 times and lethal doses calculated using the POLO computer program (Russell et al., 1977).

Neonate *T. ni* or *H. virescens* were infected using the droplet feeding assay (Hughes et al., 1986) at 2×10⁶ pibs/ml to determine the lethal time for each virus. Fifty larvae were infected with each virus. Mortality of the larvae was scored every 4, 6 or 8 hours according to the mortality rate. $LT_{50}$ values were determined using the POLO probit analysis program. Lethal Ratios for Time (LRT) were determined using AcNPV C6 as the reference strain, for comparison with other data generated in different laboratories using different bioassay techniques and conditions.

Second instar larvae of *Manduca sexta* were injected with 2×10⁴ pfu (2µl) of each recombinant virus (AcJHE, AcJHE-29, AcJHE-522 or AcJHE-29,522) and bled at 24 hour intervals post infection to assess the level of modified JHE expression in vivo. Five larvae were bled per time point per treatment. Wild type virus AcNPV C6) was injected as control. Mock infected controls injected with media (ExCell 401) were also analyzed. Hemolymph samples were diluted in PBS containing 100 µg/ml BSA and stored at −20° C. prior to assay for JHE activity (Hammock and Roe, 1985).

Pharmacokinetics

In order to establish whether the modifications made to the JHE affected the rate of uptake of the enzyme from the hemolymph by the pericardial cells, pharmacokinetic analysis was carried out. Wild type and modified JHEs harvested from cell culture were purified by DEAE anion exchange. JHE (1 nm/min) was injected into second instar *M. sexta* (30 to 38 mg) and 6 larvae per time point per treatment bled 0.3, 1, 2, 3, and 4 hours post injection. JHE activity in hemolymph samples was determined by radiochemical assay. Half lives were determined by exponential regression analysis, and rate constants of clearance calculated.

Construction of recombinant viruses expressing modified JHE

The specific alterations made in the modified JHE sequences were confirmed by sequencing. The coding sequences were introduced into the baculovirus transfer vector, pAcUW21 (FIG. 2), and the correct insertion confirmed by restriction analysis. Sf-21 cells were cotransfected with the appropriate transfer vector and AcRP8 DNA. The recombinant viruses were purified by 4 rounds of plaque purification by screening for polyhedrin positive plaques and JHE activity.

Baculovirus expression in vitro

All three mutated viruses expressing modified JHE (AcJHE-29, AcJHE-522 and AcJHE-29,522) produced active enzyme in cell culture (FIG. 3), although expression of JHE-29,522 was lower than expression of JHE, JHE-29 or JHE-522.

We found that JHE mutants having alterations at sites presumed to be involved with proteolytic degradation by the ubiquitination pathway led to greatly improved insecticidal efficiency. That is, site-directed mutagenesis significantly improved the speed of kill by baculoviruses containing some of the modified JHEs in both *H. virescens* and *T. ni*. In particular, we found larvae injected at second instar with AcJHE-29, AcJHE-522 or AcJHE-29,522 gave high level expression of JHE from 96 hours post infection (FIG. 5). Only low levels of JHE activity (less than 1 nm/min/ml) were detected in hemolymph from uninfected control larvae (injected with medium) and larvae infected with wild type virus or AcJHE.

Lethal doses were determined using the POLO program. For both *H. virescens* and *T. ni*, the LD50 values are comparable to those of the wild type virus AcNPV C6. The LD50 for AcJHE-29,522 is similar to that of the control virus AcJHE.

$LT_{50}$ data (Table 2) show that the virus AcJHE-29,522 has significantly improved $LT_{50}$ of 84 hours in *T. ni* and 80 hours in *H. virescens*, compared to 106 and 114 hours for AcNPV C6 respectively. AcJHE-29 and AcJHE-522 give slower kill than AcNPV C6 in *T. ni*, and quicker kill in *H. virescens*.

TABLE 2

Biological Activity ($LT_{50}$-hours) of Mutant JHE Expressed in AcNPV

|  | T. ni | H. virescens |
|---|---|---|
| AcNPV C6 | 106 | 114 |
| AcJHE | 107 | 118 |
| AcJHE-29 | 117 | 106 |
| AcJHE-522 | 120 | 107 |
| AcJHE-29, 522 | 84 | 80 |
| AcJHE-201 | 88 | 82 |

EXAMPLE 5

The basic protein is a 6.9K, arginine-rich polypeptide, expressed during the late phase of viral infection (10–20 hours post infection). We used the basic protein promoter in place of the polyhedrin gene in the plasmid transfer vector pAcMP1 by following a procedure described by Hill-Perkins and Possee, *Journal of General Virology*, 71, pp. 971-976 (1991). We ligated the coding sequence for juvenile hormone esterase from *Heliothis virescens* into the pAcMP1 transfer vector at the Bgl II cloning site, to produce a plasmid we called "pAcMP1JHE."

Cotransfection of the plasmid pAcMP1JHE with DNA from the virus AcUW1-PH (by the general procedure described by Weyer et al., *Journal of General Virology*, 71, pp. 1525-1534 (1990)) resulted in a basic protein-positive, polyhedrin-positive, p10-negative virus, the polyhedrin being under control of the p10 promoter at the p10 locus. JHE is expressed under control of the duplicated basic protein promoter in this virus (AcMP1JHE).

The p10 protein is expressed at high levels during the very late phase of virus infection. The p10 promoter has been inserted at the polyhedrin locus in the transfer vector pAcUW2(B) (Weyer et al., *J. Gen. Virol.*, 71, pp. 1525-1534 (1990)). We inserted the sequence for juvenile hormone esterase at the Bgl II cloning site to produce the plasmid pAcUW2(B).JHE. Cotransfection of this plasmid with DNA from AcRP8 produced a polyhedrin-positive, p10-positive virus, AcUW2(b)JHE, expressing JHE under control of a duplicated p10 promoter.

Turning to FIG. 4, one can see that the just-described plasmid pAcMP1JHE (that is, with the basic protein promoter) gave enhanced expression levels of JHE with respect to levels from the polyhedrin promoter and even with respect to levels achieved with the p10 promoter.

EXAMPLE 6

Library construction and screening

DNA was prepared from embryonic tissue derived from an outbred laboratory population of *Heliothis virescens*. In order to produce high molecular weight DNA care was taken to avoid shearing (Kaiser and Murray 1985), and consequently, the size of the purified DNA was larger than bacteriophage T4 DNA (>170 kb). The genomic library was constructed as described by Maniatis et al. (1982) and Kaiser and Murray (1985). Specifically, an optimized MboI digestion was used to partially digest the genomic DNA. The digested DNA was separated on a sucrose gradient and size-selected by pooling fractions corresponding to 10–20 kb fragments. Lambda EMBL3 arms (Stratagen) and the size-selected genomic DNA were ligated and then packaged with a commercial extract (Gigapak Gold, Stratagene).

*Escherischia coli* strain LE392 (rec $A^+$) was used to plate the library at a density of approximately 30,000 pfu per 150×15 mm petri plate. Plaques were lifted in duplicate onto nitrocellulose disks, which were prepared for hybridization by standard protocols. To screen the library, a 850 bp N-terminal Bam HI fragment from the JHE cDNA (Hanzlik et al., 1989) was labelled by random priming using hexamers (pdN6, Pharmacia) and $^{32}P$ (Amersham). After hybridization, the last wash was in 0.1× SSC at 55° C. The washed and dried filters were overlaid with XAR film (Kodak) and an intensifying screen for overnight exposure at −70° C. Positive clones, detected as duplicate signals on developed film, were isolated by a standard plaque purification protocol. A phage stock was prepared for each clone and used in the process of purifying lambda DNA on cesium chloride gradients (Maniatis et al., 1982).

Clone characterization

A hybridization experiment was conducted to determine how much of the JHE cDNA sequence was present in each of the JHE positive genomic clones. Probes from the JHE cDNA were hybridized to 5 clones which had been dot-blotted onto nylon membranes. Hybridization was performed in 7% sodium dodecyl sulfate, 1 mm EDTA and 0.5M $NaPO_4$ at 60° C. After hybridization the last wash was in 0.1× SSC at 65° C.

For further analysis, an 11 kb KpnI fragment (C11K) from genomic clone C was subcloned into pUC118. To confirm that clone C11K contained all of the JHE gene, and to aid restriction mapping of the gene, synthetic nucleotide primers were made to the sequence of the 5' and 3' ends of the full length JHE cDNA clone previously described in the parent applications and their former FIG. 2. (By "former" FIG. 2, we mean FIG. 2 of Ser. No. 07/725,226 and its predecessor Ser. No. 5 07/265,507, of which this application is a continuation-in-part. The former FIG. 2 was found to contain several minor errors in sequence, which have been corrected in the present SEQ ID NO:1.) Primer b corresponds to bases 29–46 of the JHE cDNA sequence and primer f corresponds to bases 2775–2794. A sequence kit (United States Biochemical) was used for dsDNA sequencing.

A map of clone C11K was generated to verify the linear correspondence of restriction sites, in relationship to the JHE cDNA, and for detection of introns within the genomic clone. From the 5' sequencing of C11K an NaeI restriction site was located upstream of the reading region and used to restriction map the 5' end of the gene. The 3' sequence of the genomic clone confirmed the presence of an XhoI site which was useful for mapping the 3' end of the gene. Using NaeI and XhoI sites as reference points, a map was constructed by multiple restriction endonuclease digestions with Bgl II, ClaI, NaeI, NcoI, KpnI, PstI, and XhoI. From the restriction analysis it was possible to approximate the position of introns, which were defined by synthesizing nucleotide primers complementary to the cDNA and sequencing across the intron/exon junctions.

Library construction and screening

Hybridization of the labelled JHE cDNA BamHI fragment yielded 6 positive clones in a screen of approximately 250,000 primary plaques from the genomic library. Only one of the genomic clones, C, hybridized to each of the cDNA probes and was assumed to contain most, if not all, of the JHE gene. C11K, the 11 kb Kpn fragment, was found to contain the entire JHE gene by sequence homology to the 5' and 3' termini of the JHE cDNA FIG. 6 summarizes the JHE gene, which is approximately 11 kb with four introns. Restriction sites used for the mapping of subclone C11K are represented. The exons are represented by solid regions and the introns are represented by stippling. Regions upstream and downstream of the coding region are shown as empty rectangles. The exact location of intron/exon boundaries were determined by sequencing the gene in the regions shown by restriction mapping to have introns. Primers complimentary to JHE cDNA allowed sequencing of most of the intron/exon junctions. To facilitate the sequencing of the junctions at positions 53 and 519, C11K was subcloned into two fragments at the NcoI site. Forward and reverse vector sequencing primers were then used to sequence out to intron junctions on either side of the NcoI site (*). The wedge next to the letter designation of each primer indicates the sequencing orientation from the primer. There is an ordered correspondence between restriction sites in clone C11K and sites in the JHE cDNA, indicating that the clone is representative. Four introns occur in the coding region of the gene and none are found in the 3' untranslated region. A 4.3 kb intron is located in the 19 amino acid leader sequence region, between cDNA bases 52 and 53. The possible significance of a large intron located close to the 5' end of the gene is not clear, but an analogous situation is found in the *Bombyx mori* fibroin gene. The other three introns are relatively small, ranging in size from 154 bp to 204 bp. The consensus sequences (GT-AG), common to the beginning and end of almost all introns, are present in the JHE gene.

The foregoing examples illustrate certain embodiments of the present invention, and are not intended to limit the scope of the invention, which is defined in the appended claims.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2989 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
GAATTCCCAC CGAACAGACA TGACTTCACA CGTACTCGCG CTCGCCTTCC TTCTACACGC      60
GTGCACAGCG CTGGCGTGGC AGGAGACAAA TTCGCGCAGC GTGGTCGCCC ATCTGGACTC     120
CGGCATTATA CGCGGCGTGC CGCGCTCAGC GGATGGCATC AAGTTCGCCA GCTTCCTAGG     180
AGTGCCCTAC GCTAAGCAGC CTGTTGGAGA ACTCAGGTTT AAGGAGCTCG AGCCTCTAGA     240
ACCTTGGGAT AATATCCTGA ACGCAACAAA TGAAGGACCC ATCTGCTTCC AAACAGATGT     300
ATTATACGGG AGGCTCATGG CGGCAAGCGA GATGAGCGAG GCTTGCATAT ACGCCAACAT     360
TCATGTTCCA TGGCAAAGCC TTCCCCGAGT GAGGGGGACC ACACCTTTAC GGCCTATCCT     420
GGTGTTCATA CATGGTGGAG GATTTGCTTT CGGCTCCGGC CACGAGGACC TACACGGACC     480
AGAATATTTG GTCACTAAGA ATGTCATCGT CATCACGTTT AATTACAGAT GAACGTCTT     540
CGGTTTCCTG TCCATGAACA CAACAAAAAT CCCCGGGAAT GCCGGTCTCC GGGATCAGGT     600
AACCCTGTTG CGCTGGGTGC AAAGGAACGC CAAGAATTTC GGAGGAGACC CCAGCGACAT     660
CACCATAGCG GGGCAGAGCG CTGGTGCATC AGCTGCGCAT CTACTGACTC TTTCTAAAGC     720
TACTGAAGGT CTTTTCAAAA GAGCGATTCT GATGAGCGGA ACAGGAATGA GCTACTTCTT     780
TACTACTTCT CCACTTTTCG CGGCCTACAT TTCGAAACAG TTGTTGCAAA TCCTGGGCAT     840
CAACGAGACG GATCCCGAAG AAATACATCG GCAGCTCATC GACCTACCCG CAGAGAAACT     900
GAACGAGGCT AACGCCGTCC TGATTGAACA AATTGGCCTG ACAACCTTCC TCCCTATTGT     960
GGAATCCCCA CTACCTGGAG TAACAACCAT TATTGACGAT GATCCAGAAA TCTTAATAGC    1020
CGAAGGACGC GGCAAGAATG TTCCACTTTT AATAGGATTT ACCAGCTCAG AATGCGAGAC    1080
TTTCCGCAAT CGACTATTGA ACTTTGATCT CGTCAAAAAG ATTCAGGACA ATCCTACGAT    1140
CATAATACCG CCTAAACTGT TATTTATGAC TCCACCAGAG CTGTTGATGG AATTAGCAAA    1200
GACTATCGAG AGAAAGTACT ACAACGGTAC AATAAGTATC GATAACTTCG TAAAATCATG    1260
TTCAGATGGC TTCTATGAAT ACCCTGCATT GAAACTGGCG CAAAAACGTG CCGAAACTGG    1320
TGGAGCTCCA CTGTACTTGT ACCGGTTCGC GTACGAGGGT CAGAACAGCA TCATCAAGAA    1380
GGTAATGGGG CTGAACCACG AGGGTGTCGG CCACATTGAG GACTTAACCT ATGTGTTTAA    1440
```

-continued

```
GGTCAACTCT ATGTCCGAAG CTCTGCACGC ATCGCCTTCT GAGAATGATG TGAAAATGAA    1500
GAATCTAATG ACGGGCTATT TCTTAAATTT TATAAAGTGC AGTCAACCGA CATGCAAGA     1560
CAATAACTCA TTGGAGGTGT GGCCGGCTAA CAACGGCATG CAATACGAGG ACATTGTGTC    1620
TCCCACCATC ATCAGATCCA AGGAGTTCGC CTCCAGACAA CAAGACATTA TCGAGTTCTT    1680
CGACAGCTTC ACCAGTAGAA GCCCGCTTGA ATGATAAGAC TGAACTATTG TCATCGATAT    1740
AAATATGTTG TTAATGTTAG TTAAGAGTTC TCATAGTGCA GTGAGCGTTT GAACTGAACC    1800
ACTGGTCTCA GAAGATCGAA GTTCATCCT ATGACATAAG AGTGTACAAT GTTTTCAGTT     1860
AAGTGTTGAT GTTGATACTT TAATTTGCAT TAATTTATTT AGAGTAAGGT TAATGTCACA    1920
AGTCTAGTCG GTTACTTAAG TAATTTCTTG CCAACATTGG TGTAATGCCT TTTCGTTGAG    1980
TTTCAAAAAA TATTAATATT ATATGCATTA TAAATTAAAT TCTAATTTTC ATCGTAGAAT    2040
ATAATACCAT AGTTAGCATT GTTGCTCTTT GAGAAGAGGT CAATGCCCAG CAATAGGAAA    2100
GTACAAAGGT CGATGATGAT GAATAAGCAG ATAAATTATA GAGCTTCTAC TTCATTGATG    2160
TTGATTGAAA CTCATGTTGA CATCTTTGTG AAATCATTTG ACATCAAAGA GAACATAACT    2220
TTAGTTTAAC GACACGGATT TACTATTAGG AACAGCTAGA CCTTCTTTAG ACCTAGTATT    2280
GTTTTACGAA GCAATTGTAA TAAAACTTGG GTGAAAATAA AGGTTAGTCG TAATTACAGC    2340
ATTACGACTA AGCTTTGTTA GTGCCCGGAA GATTGATCTC ATAAAACTAC ACTAGGCTAT    2400
GGATAACAAT CCGCCCGCAA TTTAATTTTA AGTTAATATA AGTTATTTTG AAAATTATAT    2460
TTTTGTACAA AATGCTGCAG ATCACGGGAC GTCTATTCGA TTTGATATTC GAAAAGGAAT    2520
TTTACTATTT TGACTTTCGA GAGTCTGACG AGATGTTAGT ATATTCGCGA GCATCCATAA    2580
ATCGAATTTG TGTTAATTGG AAGTTCGTTC TCGATCTAGA TTCGTAAGGT GCATGGTGCT    2640
ACTTACTAGA TAAATATTAG CAATACAATT GAATTTCGTA TTCCAAAACT ATCCCTATTC    2700
CTGATTACGA AGGGCAGTGT ACAAAATAGT GAAAAATTGT AATTGTACAG AATGATAATC    2760
CCGTGATCCA AGCACTCGAG ATGCGTAATG AAGCGACTGA TGTAACGTAT TATAATTTAA    2820
GTCAATTTAC TATTAGTTTT CAACGCCTTT GTAAATATTT CACTTTCTAA TGTAATTTTA    2880
GTATTCCCGC ACAATGACGC CAGAGTACAA TGATCGGACG CGATCGCGTG GCGTTACATT    2940
TAATGATTCA AATAAATAAT TGCGTCGGAC GGACGTGAAA AAAAAAAAA                2989
```

( 2 ) INFORMATION FOR SEQ ID NO:2:

( i ) SEQUENCE CHARACTERISTICS:
        ( A ) LENGTH: 3047 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

```
GAATTCCAAC AGACATGACT TCACACGTAC TCGCGCTCGC CTTCTTTCTA CACGCGTGCA     60
CAGCGCTGGC GTGGCAGGAG ACAAATTCGC GCAGCGTGCT CGCCCATCTG GACTCCGGCA    120
TTATACGCGG CGTGCCGCGC TCAGCGGATG GCATCAAGTT CGCCAGCTTC CTAGGAGTGC    180
CCTACGCTAA GCAGCCTGTT GGAGAACTCA GGTTTAAGGA GCTCGAGCCT CTAGAACCTT    240
```

| | | | | | |
|---|---|---|---|---|---|
| GGGATAATAT | CCTGAACGCA | ACAAATGAAG | GACCCATCTG | CTTCCAAACA | GATGTATTAT | 300
| ACGGGAGGCT | CATGGCGGCA | AGCGAGATGA | GCGAGGCTTG | CATATACGCC | AACATTCATG | 360
| TTCCATGGCA | AAGCCTTCCC | CGAGTGAGGG | GGACCACACC | TTTACGGCCT | ATCCTGGTGT | 420
| TCATACATGG | TGGAGGATTT | GCGTTCGGCT | CCGGCCACGA | GGACCTACAC | GGACCAGAAT | 480
| ATTTGGTCAC | TAAGAATGTC | ATCGTCATCA | CGTTTAATTA | CAGATTGAAC | GTCTTCGGTT | 540
| TCCTGTCCAT | GAACACAACA | AAAATCCCCG | GAATGCCGG | TCTCCGGGAT | CAGGTAACCC | 600
| TGTTGCGCTG | GGTGCAAAGG | AACGCCAAGA | ATTTCGGAGG | AGACCCCAGC | GACATCACCA | 660
| TAGCGGGGCA | GAGCGCTGGT | GCATCAGCTG | CGCATCTACT | GACTCTTTCT | AAAGCTACTG | 720
| AAGGTCTTTT | CAAAAGAGCG | ATTCTGATGA | GCGGAACAGG | AATGAGCTAC | TTCTTTACTA | 780
| CTTTCTCCAC | TTTTCGCGGC | CTACATTTCG | AAACAGTTGT | TGCAAATCCT | GGCATCAAC | 840
| GAGACGGATC | CCCGAAGAAA | TACATCGGCA | GCTCATCGAC | CTACCCGCCG | AGAAACTGAA | 900
| CGAGGCTAAC | GCCGTCCTGA | TTGAACAAAT | TGGCCTGACA | ACCTTCGTCC | CTATTGTGGA | 960
| ATCCCCACTA | CCTGAAGTAA | CAACCATTAT | TGACGATGAT | CCAGAAATCT | TAATAGCCGA | 1020
| AGGACGCGGC | AAGAATATTC | CACTTTTAAT | AGGATTTACC | AGCTCAGAAT | GCGAGACTTT | 1080
| CCGCAATCGA | CTATTGAACT | TTGATCTCGT | CAAAAAGATT | CAGGACAATC | CTACGATCAT | 1140
| AATACCGCCT | AAACTGTTAT | TTATGACTCC | ACCAGAGCTG | TTGATGGAAT | TAGCAAAGAC | 1200
| TATCGAGAGA | AAGTACTACA | ACGGTACAAT | AAGTATCGAT | AACTTCGTAA | AATCATGTTC | 1260
| AGATGGCTTC | TATGAATACC | CTGCATTGAA | ACTGGCGCAA | AAACGTGCCG | AAACTGGTGG | 1320
| AGCTCCACTG | TACTTGTACC | GGTTCGCGTA | CGAGGGTCAG | AACAGCATCA | TCAAGAAGGT | 1380
| AATGGGGCTG | AACCACGAGG | GTGCCGGCCA | CATTGAGGAC | TTAACCTACG | TGTTTAAGGT | 1440
| CAACTCTATG | TCCGAAGTTC | TGCACGCATC | GCCTTCTGAG | AATGATGTGA | AAATGAAGAA | 1500
| TCTAATGACG | GGCTATTTCT | TAAATTTTAT | AAAGTGCAGT | CAACCGACAT | GCGAAGACAA | 1560
| TAACTCACTG | GAGGTGTGGC | CGGCTAACAA | CGGCATGCAA | TACGAGGACA | TTGTGTCTCC | 1620
| CACCATCATC | AGATCCAAGG | AGTTCGCCTC | CAGACAACAA | GACATTATCG | AGTTCTTCGA | 1680
| CAGCTTGTCC | AGTAGAAGCC | CACTTGAATG | ATAAGACTGA | ACTATTGTCA | TCGATATAAA | 1740
| TATGTTGTTA | ATGTTAGTTA | AGAGTTCTCA | TAGTGCAGTG | AGCGTTTGAA | CTGAACCACT | 1800
| GGTCTCAGAA | GATCGAAGTT | TCATCCTATG | ACATAAGAGT | GTACAATGTT | TTCAGTTAAG | 1860
| TGTTGATGTT | GATACTTTAA | TTTGCATTAA | TTTATTTAGA | GTAAGGTTAA | TGTCACAAGT | 1920
| CTAGTCGGTT | ACTAAAGTAA | TTTCTTGCCA | ACATTGGTGT | AATGCCTTTT | CGTTGAGTTT | 1980
| CAAAAAATAT | TATTATTATA | TGCATTTTAA | ATTAAATTCT | AATTTTCATC | GTAGAATACA | 2040
| ATACCATAGT | TAGCATTGTT | GCTCTTTGAG | AAGAGGCCAA | TGCCCAGCAA | TAGGAAAGTA | 2100
| CAAAGGTCGA | TGATGATGAA | TAAGCAGATA | AATTATAGAG | CTTCTACTTC | ATTGATATTG | 2160
| ATTGAAACTC | ATGTTGACAT | CTTTGTGAAA | TCATTGACA | TCAAAGAGAA | CATAACTTTA | 2220
| GTTAACGAC | ACGGATTTAC | TATTGAAACA | GCTAGACCTT | CTTTAGACCT | AGTATTGTTT | 2280
| TACGAAGCAA | TTGTAATAAA | ACTTGGGTGA | AAATAAAGGT | TAGTCGTAAT | TACAGCATTA | 2340
| CGACTAAGCT | TTGTTAGTGC | CCGGAAGATT | GATCTCATAA | AACTACACTA | GGCTATGGAT | 2400
| AACAATCCGC | CCGCAATTTA | ATTTTAAGTT | AATATAAGTT | ATTTTGAAAA | TTATATTTTT | 2460
| GTACAAAATG | CTGCAGATCA | CGGGACGTCT | ATTCGATTTG | ATATTCGAAA | AGGAATTTAA | 2520
| CTATTTTGAC | TTTCGAGAGT | CTGACGTGAT | GTTAGTATAT | TCGCGAGCAT | CCATAATTAA | 2580
| CTATTTTGAC | TTTCGAGAGT | CTGACGTGAT | GTTAGTATAT | TCGCGAGCAT | CCATAAATCG | 2640

-continued

| | | | | | | |
|---|---|---|---|---|---|---|
| AATTTGTGTT | AATTGGAAGT | TCGTTCTCGA | TCTAGATTCG | TAAGGTGCAT | GGTGCTACTT | 2700 |
| ACTAGATAAA | TATTAGCAAT | ACAATTGAAT | TTCGTATTCC | AAACGAAGGG | CAGTGTACAA | 2760 |
| AATAGTGAAA | AATTGTAATT | GTACAGAATG | ATAATCCCGT | GATCCAAGCA | CTCGAGATGC | 2820 |
| GTAATGAAGC | GACTGATGTA | ACGTATTATA | ATTAAGTCA | ATTTACTATT | AGTTTTCAAC | 2880 |
| GCCTTTGTAA | ATATTTCACT | TTCTAATGTA | ATTTAGTAT | TCCCGCACAA | TGACGCCGAG | 2940 |
| TACAATGATC | GGACGCGATC | GCGTGGCGTT | ACATTTAATG | ATTCAAATAA | ATAATTGCGT | 3000 |
| CGGACGGACG | TGGAAAAAAA | AAAAAAAAA | AAAAAAAAA | AAAAAA | | 3047 |

It is claimed:

1. A recombinant virus having a nucleotide sequence for a juvenile hormone esterase or a mutant thereof, wherein the expression of the nucleotide sequence results in juvenile hormone esterase or a mutant thereof capable of degrading insect juvenile hormone with a $k_{cat}/K_m$ ratio greater than about $10^8$, the nucleotide sequence being as in SEQ ID NO:1 or SEQ ID NO:2 or a mutated sequence thereof, the mutated sequence coding for a substituted amino acid reside at one or more of lysine positions 29 and 522 or serine 201.

2. The recombinant virus as in claim 1 wherein the virus is a baculovirus.

3. The recombinant virus as in claim 2 wherein the baculovirus is a nuclear polyhedrosis virus.

4. The recombinant virus as in claim 2 wherein the baculovirus is *Autographa californica.*

* * * * *

UNITED STATES PATENT AND TRADEMARK OFFICE
CERTIFICATE OF CORRECTION

PATENT NO. : 5,674,747
DATED : October 7, 1997
INVENTOR(S) : Bruce D. Hammock et al.

It is certified that error appears in the above-identified patent and that said Letters Patent is hereby corrected as shown below:

On the title page:

Section [56] References Cited, Other Publications, page 3 replace:

"Bonning et al., "Superior Expression of JHE and α-Galac-"

with

--Bonning et al., "Superior Expression of JHE and β-Galac-

Column 3, Line 59 replace:

"hormone seterases, but purification of the low abundance"

with

--hormone esterases, but purification of the low abundance-

Column 5, Line 20 replace:

"The recent development of a vital expression vector from"

with

--The recent development of a viral expression vector from--

UNITED STATES PATENT AND TRADEMARK OFFICE
CERTIFICATE OF CORRECTION

PATENT NO. : 5,674,747
DATED : October 7, 1997
INVENTOR(S) : Bruce D. Hammock et al.

It is certified that error appears in the above-identified patent and that said Letters Patent is hereby corrected as shown below:

Column 12, Line 66, replace:
    "sequence of clone 3hv21 are indicted to be Leu and Pro," with --sequence of clone 3hv21 are indicated to be Leu and Pro,--

Column 13, TABLE 1, Line 10 replace:
    "4       Thr (Gln)      100 (320)" with --4      Thr (Gln)      100 (310)--

Column 16, Line 48 replace:
    "mids and the vital DNA resulted in polyhedrin positive" with --mids and the viral DNA resulted in polyhedrin positive--

Signed and Sealed this

Twenty-third Day of June, 1998

Attest:

BRUCE LEHMAN

Attesting Officer     Commissioner of Patents and Trademarks